(12) United States Patent
Park et al.

(10) Patent No.: US 8,974,819 B2
(45) Date of Patent: Mar. 10, 2015

(54) SUSTAINED-RELEASE CHITOSAN CAPSULES COMPRISING CHITOSAN AND PHYTIC ACID

(71) Applicant: Industry-Academic Cooperation Foundation, Yonsei University, Seoul (KR)

(72) Inventors: Ji Yong Park, Goyang-si (KR); Chan Min Jeong, Anyang-si (KR); Min Kyung Lee, Seoul (KR); Sung Won Choi, Seoul (KR); Young Hee Cho, Yongin-Si (KR); Hoon Ok Jeong, Inje-gun (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 122 days.

(21) Appl. No.: 13/656,378

(22) Filed: Oct. 19, 2012

(65) Prior Publication Data

US 2013/0045275 A1    Feb. 21, 2013

Related U.S. Application Data

(62) Division of application No. 12/674,365, filed as application No. PCT/KR2008/003015 on May 29, 2008, now abandoned.

(30) Foreign Application Priority Data

Jun. 18, 2007   (KR) .......................... 10-2007-0059470
May 27, 2008   (KR) .......................... 10-2008-0049040

(51) Int. Cl.
*A61K 9/48*     (2006.01)
*A61K 31/70*    (2006.01)
*A61K 9/00*     (2006.01)
*A61K 9/50*     (2006.01)
*A61K 31/7088*  (2006.01)

(52) U.S. Cl.
CPC .............. *A61K 31/70* (2013.01); *A61K 9/0053* (2013.01); *A61K 9/5036* (2013.01); *A61K 31/7088* (2013.01)
USPC ....................................................... 424/451

(58) Field of Classification Search
None
See application file for complete search history.

(56) References Cited

U.S. PATENT DOCUMENTS

| | | | |
|---|---|---|---|
| 4,066,568 A * | 1/1978 | Nakazawa et al. | 427/213.3 |
| 4,803,168 A | 2/1989 | Jarvis, Jr. | |
| 5,468,503 A * | 11/1995 | Yamada et al. | 424/461 |
| 2002/0150624 A1 | 10/2002 | Watanabe et al. | |
| 2003/0195246 A1 * | 10/2003 | Nakamura et al. | 514/469 |
| 2004/0167323 A1 | 8/2004 | Chan et al. | |
| 2008/0311214 A1 | 12/2008 | Rao | |
| 2009/0030091 A1 | 1/2009 | Shiraishi et al. | |
| 2010/0173002 A1 * | 7/2010 | Yulai et al. | 424/492 |

FOREIGN PATENT DOCUMENTS

| | | | |
|---|---|---|---|
| EP | 0 460 921 A2 | | 11/1991 |
| EP | 0460921 A2 * | | 12/1991 |
| KR | 2000-18339 A | | 4/2000 |
| KR | 2001-0025930 A | | 4/2001 |
| KR | 2002072600 A * | | 9/2002 |
| WO | WO 2005/041885 A2 | | 5/2005 |

OTHER PUBLICATIONS

International Search Report mailed Aug. 27, 2008.
Shu et ;al., "The Influence of Multivalent Phosphate Structure on the Properties of Ionically Cross-Linked chitosan Filmes for Controlled Drug Release", European Journal of Pharmaceutics and Biopharmaceutics, vol. 54, Issue 2, Sep. 2002, pp. 235-243 (Abstract only).
Welsh et al., "Chitosan Cross-Linking With a Water-Soluble, Blocked Diisocyanate.2.Solvates and Hydrogels", Biomacromolecules, vol. 4, No. 5, 2003, pp. 1357-1361.

* cited by examiner

*Primary Examiner* — Susan Tran
(74) *Attorney, Agent, or Firm* — Birch, Stewart, Kolasch & Birch, LLP

(57) ABSTRACT

The present invention relates to a chitosan capsule in which a soluble active ingredient is encapsulated in a matrix containing chitosan and phytic acid; a cross-linking method and materials capable of being used in preparing the capsule; and pharmaceutical, food and cosmetic compositions comprising the capsule. The chitosan capsule according to the present invention is prepared via ionic gelation of chitosan as a biodegradable polymer with phytic acid capable of rapidly and effectively forming a cross-linking reaction with the chitosan polymer. The capsule of the present invention shows high encapsulation efficiency for a soluble active ingredient and protects the soluble active ingredient from being damaged in a digestive tract, resulting in improving an in vivo delivery efficiency of a physiologically active material. Further, since the capsule of the present invention has a pH-dependent sustained-release mechanism which can minimize the release of a soluble active ingredient in the stomach and gradually release in the intestine, it is possible to regulate sustained-release of a soluble active ingredient.

11 Claims, 26 Drawing Sheets

Fig. 11

| Chitosan | Concentration of insulin (%) | Entrapment efficiency (%) | |
|---|---|---|---|
| | | Mean | Standard deviation |
| Ch-A | 3 | 100.0 | ±0.0 |
| | 5 | 65.4 | ±5.5 |
| | 10 | 38.5 | ±7.1 |
| | 15 | 14.8 | ±4.3 |

Fig. 12

| Chitosan | pH of TPP solution | Concentration of TPP | Efficiency |
|---|---|---|---|
| Ch-A | 3 | 4 | 86.3±4.9 |
| | 3 | 5 | 86.1±2.5 |
| | 3 | 6 | 89.8±2.9 |
| | 3 | 7 | 88.5±3.5 |
| | 5 | 4 | 83.0±3.2 |
| | 5 | 5 | 87.4±1.5 |
| | 5 | 6 | 89.2±1.4 |
| | 5 | 7 | 88.1±4.1 |
| | 7 | 4 | 91.4±3.0 |
| | 7 | 5 | 92.4±1.4 |
| | 7 | 6 | 93.3±2.3 |
| | 7 | 7 | 87.5±2.1 |

Fig. 19

| Formulation | AAC$_{0-48}$$^a$ | C$_{max}$$^b$(%) | t$_{max}$$^c$(h) | F$^d$(%) |
|---|---|---|---|---|
| Insulin-contained chitosan capsule-A (6%, pH 1.0 of PA) | 1941.5±45.7 | 57.6±4.3 | 18 | 6.4±0.8 |
| Insulin-contained chitosan capsule-B (6%, pH 6.0 of PA) | 1942.5±67.4 | 58.9±5.8 | 6 | 6.4±0.6 |
| Insulin-contained chitosan capsule-C (6%, pH 7.0 of TPP) | 327.5±23.1 | 21.4±8.0 | 1 | 1.1±0.3 |
| Subcutaneous injections | 749.5±37.7 | 84.3±3.6 | 1 | 100 |

SUSTAINED-RELEASE CHITOSAN CAPSULES COMPRISING CHITOSAN AND PHYTIC ACID

This application is a Divisional of copending application Ser. No. 12/674,365 filed on Feb. 19, 2010, which is the U.S. National Phase of PCT/KR2008/003015, filed May 29, 2008, and which claims priority to Application No. 10-2007-0059470 filed in Korea, on Jun. 18, 2007, and Application No. 10-2008-0049040 filed in Korea on May 27, 2008. The entire contents of all of the above applications are hereby incorporated by reference.

TECHNICAL FIELD

The present invention relates to a chitosan capsule in which a soluble active ingredient is encapsulated in a matrix containing chitosan and phytic acid, a method of preparing the capsule, and pharmaceutical, food and cosmetic compositions comprising the capsule. Since the chitosan capsule of the present invention is formed via ionic gelation reaction of chitosan as a biodegradable polymer with phytic acid capable of rapidly and effectively forming a cross-linking reaction with the chitosan polymer, it is possible to encapsulate 90% or more of a soluble active ingredient and to improve an in vivo delivery efficiency of an active ingredient by preventing it from being damaged in an acidic condition of stomach and exhibiting a sustained-release mechanism which implies appropriate slow release of the active ingredient over a long period.

BACKGROUND ART

For an effective in vivo delivery, digestion and absorption of a soluble active ingredient, there is a need for a control system which can protect the encapsulated soluble active ingredient in the stomach under high acidic conditions with a low pH, and can release the content slowly in the intestinal tract requiring relatively long retention time. The encapsulation of an active ingredient is essential to achieve the control system. Encapsulation technique is a process by which a soluble active ingredient in a solid, a liquid or a gas state is coated with or entrapped within another material or system so that the soluble active ingredient is released under specific conditions. Generally, synthetic or natural polymers are used as a capsule material.

Chitosan is a natural cationic polysaccharide produced by deacetylation of chitin and has excellent biodegradable and biocompatible characteristics with low toxicity [*J. Microencapsulation* 2000, 17, 625~638]. It has a good gel and film forming character and can easily bind with anionic materials due to its multivalent cations [*J. Chem. Technol. Biotechnol.* 1990, 49, 395~404], and it shows excellent mucoadhesiveness to mucosal tissues such as intestinal tract [*J. Pharm. Sci.* 2003, 92, 567~576]. Therefore several researches on the effective in vivo delivery of pharmaceuticals or functional materials via encapsulation using chitosan has been conducted.

An emulsion cross-linking method [*Int. J. Pharm.* 1994, 11, 217~222], an emulsion droplet coalescence method [*Pharm. Res.* 1999, 16, 1830~1835], a reverse micellar method [*J. Controlled Release* 2001, 17, 317~323], a spray-drying method [*Int. J. Pharm.*, 1994, 217~222], an O/W/O multiple emulsion method [Korean Patent Application No. 10-2005-0014831] and the like have been broadly used to prepare the capsule using chitosan.

Since chitosan itself cannot be used to prepare a capsule, ionic gelation methods have been developed to form a capsule within a short period through a rapid cross-linking reaction between multivalent cationic chitosan and anionic counter-ions as a cross-linking agent. The ionic gelation can form an insoluble membrane on the surface of the polymer via the cross-linking reaction, and the encapsulation process is completed through a phase separation. The capsules prepared as above are composed of synthetic or natural polymers and provide controlled release of the content. The release rate of the content is controlled by chemical structure, thickness and size of the capsule membrane, the concentration of the ingredient composing the capsule, the concentration of the content, the concentration of cross-linking agents, a media pH and the like [*Int. J. Pharm.* 2004, 274, 1~33; *J. Controlled Release*, 2004, 150, 5~28].

As a cross-linking agent added for the ionic gelation of chitosan, glutaraldehyde and sulfuric acid have been used [*J. Microencapsulation* 1998, 15, 373~382; *J. Microencapsulation* 2002, 19, 173~180; Korean Patent Nos. 10-1998-0056584 and 10-2003-0085599]. However, due to their toxicity it is impossible to apply glutaraldehyde and sulfuric acid directly to foods, and they are only restrictively used in a pharmaceutical field.

Recently, there have been developed techniques of preparing a chitosan capsule by using a low toxic cross-linking agent for in vivo drug delivery. Moliaro et al. [*Biomaterials* 2002, 23, 2717~2722] and Eve Ruel-Gariepy et al. [*European J. Pharmaceutics and Biopharmaceutics* 2004, 57, 53~63] have developed a drug delivery system capable of forming a chitosan gel through heat treatment by adding glycerolphosphate which can provide a counter-ion to a chitosan solution. Besides, there are several cross-linking agents for chitosan, for example, alginic acid [U.S. Pat. No. 6,365,187 B2; U.S. Pat. No. 6,534,091 B1] and polymers such as sodium carboxymethyl cellulose and xanthan gum [Korean Patent Publication No. 2006-0016164, Korean Patent Publication No. 2001-0025930]. Particularly, it is a general trend that a chitosan capsule is prepared by using tripolyphosphate (TPP) as a cross-linking agent [*Int. J. Pharm.* 2002, 249, 165~174; *J. Pharm. Sci.* 2002, 91, 1396~1404; *Int. J. Pharm.* 2003, 250, 215~226; *Int. J. Pharm.* 2006, 311, 187~195]. However, such methods have problems of a low encapsulation yield, a complicated manufacturing process, excessive release and degradation of a drug in the stomach, excessive inhibition of drug release, or the like. Thus, although the use of chitosan for the encapsulation of a soluble active ingredient has many advantages as described above, its commercialization and application are restricted. Therefore, it is necessary to prepare a chitosan capsule using a new type of a cross-linking agent to achieve a high encapsulation yield and a protection against high acidity in the stomach while a gradual release of an active ingredient in the intestine.

DISCLOSURE

Technical Problem

The present invention is conceived to solve the aforementioned problems in the prior art. An object of the present invention is to provide a sustained-release chitosan capsule through the establishment of a rapid and effective cross-linking system using chitosan and multivalent anionic phytic acid as a cross-linking agent having low toxicity, whereby the chitosan capsule has a high encapsulation efficiency, prevents a soluble active ingredient from being damaged, exhibits high stability in the stomach and sustained releases of the encapsulated soluble active ingredients in the intestine.

Another object of the present invention is to provide a method of cross-linking cationic biocompatible polymers by using phytic acid and a method of preparing a sustained-release chitosan capsule by using the above method.

A further object of the present invention is to provide pharmaceutical, food and cosmetic compositions comprising the sustained-release chitosan capsule.

Technical Solution

The present invention provides a chitosan capsule wherein a soluble active ingredient is encapsulated within a matrix containing chitosan and phytic acid.

The present invention also provides a method of cross-linking biocompatible polymers by using phytic acid.

Further, the present invention provides a method of preparing a chitosan capsule comprising a first step of preparing an aqueous solution containing chitosan and a soluble active ingredient; a second step of preparing an aqueous solution containing phytic acid; and a third step of bringing the aqueous solution prepared in the first step into contact with the aqueous solution prepared in the second step to perform ionic gelation.

Furthermore, the present invention provides pharmaceutical, food and cosmetic compositions comprising the chitosan capsule.

Advantageous Effects

The chitosan capsule prepared according to the present invention shows a high encapsulation efficiency of a soluble active ingredient and protects the soluble active ingredient from being damaged, thereby improving an in vivo delivery efficiency of a physiological active material. Further, the chitosan capsule maintains high stability of an encapsulated soluble active ingredient under acidic conditions in the stomach and exhibits a sustained-release effect under neutral conditions in the intestine. Therefore, it is possible to significantly increase in vivo bioavailability of an encapsulated soluble active ingredient through sustained-release at the digestive organ and to effectively apply the chitosan capsule to various industrial fields including medicinal formulations, foods or cosmetics.

DESCRIPTION OF DRAWINGS

FIG. 11 is a graph showing an encapsulation efficiency of insulin depending on a concentration of insulin solution in a chitosan-phytic acid capsule prepared according to Example 3.

FIG. 12 is a graph showing an insulin encapsulation efficiency of the chitosan-tripolyphosphate capsule depending on a concentration and pH of tripolyphosphate in a chitosan-tripolyphosphate capsule prepared according to Comparative Example 2.

FIG. 19 is a graph numerically illustrating the results of FIG. 18.

MODE FOR INVENTION

Figure 1:
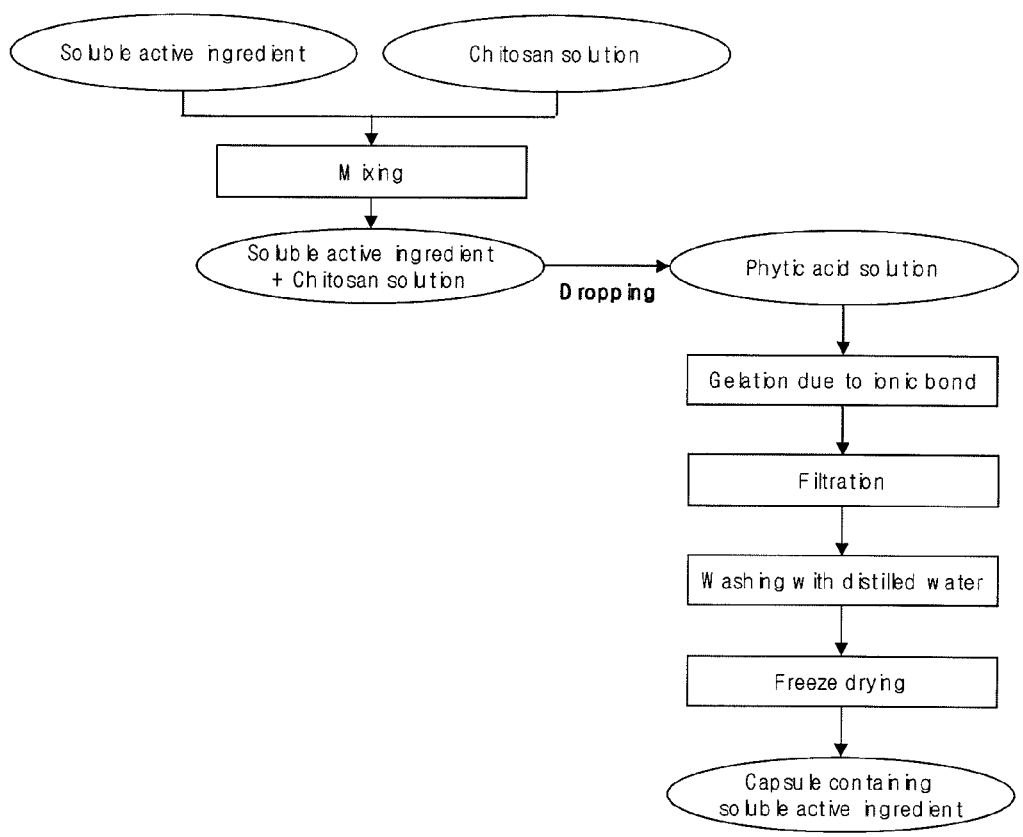
FIG. 1 is a diagram illustrating a process of preparing a chitosan capsule according to an embodiment of the present invention.

The present invention relates to a chitosan capsule comprising a soluble active ingredient encapsulated in a matrix containing chitosan and phytic acid. The chitosan capsule of the present invention is characterized in that it shows a high encapsulation efficiency for the soluble active ingredient, improves an in vivo delivery efficiency of the active ingredient by preventing it from being damaged and exhibiting a pH-dependent sustained-release effect thereof.

Hereinafter, the chitosan capsule in accordance with the present invention will be described in detail.

There is no limitation on the kind of a soluble active ingredient to be encapsulated in an encapsulating matrix. The soluble active ingredients of the present invention may include all kinds of materials that can be dissolved in water regardless of their functions and molecular structures, and preferably exemplified by one or more of pharmaceutically active ingredients, food active ingredients and cosmetically active ingredients. Since chitosan and phytic acid contained in a matrix show high biostability, the chitosan capsule improves an in vivo delivery efficiency of an active ingredient by preventing it from being damaged. Also, the chitosan capsule exhibits a pH-dependent sustained-release effect, thereby delivering and releasing the encapsulated active ingredient to the intestine while stably maintaining it in the stomach. Thus, the chitosan capsule can maximize in vivo absorption of the active ingredient. The chitosan capsule of the present invention can be effectively applied to foods, medicinal formulations, cosmetics and the like, and thus, exhibit significantly improved efficacy. Further, there is no limitation on the kind of an active ingredient used, and all kinds of active ingredients conventionally used in food, medicine and cosmetic fields can be used without limitation. Examples of such active ingredients may include nucleic acids, amino acids, peptides, proteins, sugars, carbohydrates, lipids, glycolipids, plant-, animal- or microorganism-derived compounds, plant extracts, synthetic compounds, vitamins, microorganisms, viruses, a mixture thereof and the like, but are not limited thereto. Examples of the peptides or proteins may include serum proteins, human growth hormone, interferon, colony stimulating factor, interleukin, macrophage activating factor, B cell factor, T cell factor, Protein A, allergy inhibitory factor, cell necrosis glycoprotein, immunotoxin, lymphotoxin, tumor necrosis factor, tumor suppressor factor, transforming growth factor, alpha-1 antitrypsin, albumin, apolipoprotein-E, erythropoietin, Factor VII, Factor VIII, Factor IX, plasminogen activating factor, urokinase, streptokinase, Protein C, C-reactive protein, superoxide dismutase, platelet-derived growth factor, epidermal growth factor, osteogenesis-promoting protein, insulin, atriopeptin, cartilage inducer, connective tissue activating factor, follicle-stimulating hormone, luteinizing hormone, nerve growth factor, relaxin, somatomedin, insulin-like growth factor, cholecystokinin, monoclonal or polyclonal antibodies to virus, monoclonal or polyclonal antibodies to bacteria, monoclonal or polyclonal antibodies to toxin and virus-derived vaccine antigens. The above listed peptides or proteins may include naturally occurring products, artificially synthesized products, and recombinantly engineered products. Further, besides the above listed peptides or proteins, their analogs or mutants modified by various methods such as addition, substitution or deletion of amino acids or domains or glycosylations are included within the present invention. As the soluble active ingredients, examples of the vitamins may include water-soluble vitamins such as vitamin B and its derivatives and vitamin C and its derivatives; those of the plant extracts may include saponin of a wild ginseng, a ginseng or a red ginseng, isoflavone, flavonoid, resveratrol, etc.; those of the microorganism-derived compounds may include kojic acid and its derivatives, polyglutamic acid, levan, etc.; and those of the microorganisms may include lactobacillus, etc.

There is no limitation on the kind of chitosan used in the present invention, but it is preferable to use a linear polysaccharide comprising D-glucosamine as a deacetylation unit and N-acetyl-D-glucosamine as an acetylation unit. Examples of such a chitosan may include poly[β-(1-4)-2-amino-2-dioxy-D-glucopyranose] and its derivatives. Examples of the chitosan derivatives may include thiolated chitosan, trimethylated chitosan, carboxymethyl chitosan, N-(2-hydroxyl propyl-3-trimethyl ammonium) chitosan chloride and the like. Preferably, the chitosan suitable for the present invention may have an average molecular weight ranging from 30,000 to 1,000,000 daltons, more preferably, 80,000 to 300,000 daltons. In case of using chitosan having an average molecular weight lower than 30,000 daltons, because of too low viscosity of a chitosan solution, it is apprehended that an encapsulation yield lowers. On the other hand, when the average molecular weight of chitosan exceeds 1,000,000 daltons, a chitosan solution exhibits too high viscosity, which may bring out difficulty in proceeding encapsulation.

The matrix of the chitosan capsule according to the present invention comprises phytic acid in addition to chitosan, which functions to cross-link chitosan polymers as a cross-linking agent. Phytic acid is contained in all kinds of plants, in particular seeds and grains, and has a property of forming a neutral salt via binding with an alkali. Phytic acid which is also called myo-inositol hexaphosphate is composed of six molecules of phosphates coupled to a myo-inositol ring via an ester bond, wherein the phosphates are symmetrically coupled thereto as illustrated in Formula 1. As comparing the structure of phytic acid with that of tripolyphosphate represented by Formula 2 which has been widely used as a cross-linking agent for a biocompatible polymer such as chitosan, it has been found that anions in phytic acid capable of reacting with cations of chitosan are two or more times as much as those in tripolyphosphate.

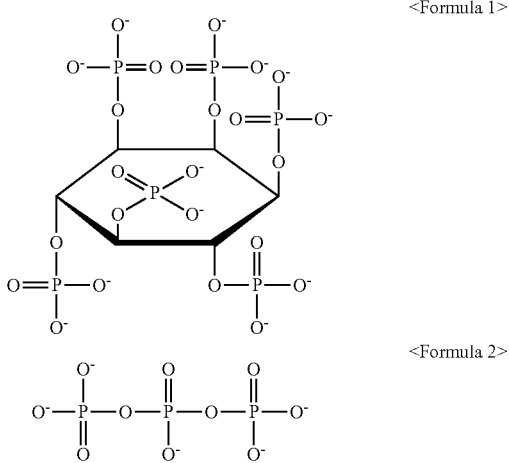

<Formula 1>

<Formula 2>

Since the chitosan capsule of the present invention uses phytic acid which is safe as a bioactive ingredient and comprises many anions capable of reacting with chitosan, it is possible to show enhanced reactivity with chitosan and provide in vivo stability. The chitosan capsule of the present invention has a firm structure having a few pores according to a rigid binding of chitosan with phytic acid. Such a structure of the chitosan capsule can not only increase the encapsulation efficiency of an active ingredient but also prevent a digestive enzyme, which can degrade a physiologically active material in digestive tract mucosa and/or the slime layer distributed in its upper part, from approaching to the active ingredient, thereby making it possible to prevent the active ingredient from being damaged by an digestive juice. In particular, when the active ingredient to be delivered is a protein, the chitosan capsule of the present invention prevents the protein from being in contact with a protease existing in the digestive tract, thereby protecting the active ingredient. As stated above, the capsule of the present invention increases the encapsulation efficiency of an active ingredient and prevents the damage of an active ingredient, which results in improving an in vivo delivery efficiency of an active ingredient.

Further, the chitosan capsule of the present invention has a characteristic of pH-dependent sustained-release. In particular, since the chitosan capsule of the present invention is very stable under acidic conditions, when orally administered, it does not release the encapsulated soluble active ingredient under low pH conditions such as in the stomach, but gradually releases the same under neutral conditions such as in the small intestine.

Also, the present invention provides a method of cross-linking biocompatible polymers by using phytic acid. The biocompatible polymer is preferably a cationic polymer, which is exemplified by chitosan used as a biocompatible polymer in the present invention.

As described above, phytic acid has anions two or more times as much as tripolyphosphate which is frequently used as a cross-linking agent for a conventional biocompatible cationic polymer. Therefore, phytic acid can be used effectively in the cross-linking reaction with cationic counter ions, for example, ionic gelation reaction, etc. Such an ionic gelation reaction is usually employed when preparing a capsule by using a biocompatible polymer such as chitosan and is a method of forming a capsule within a short time through a rapid reaction of a cationic biocompatible polymer with a cross-linking agent having a counter ion thereto. Phytic acid has been regarded in the past as an anti-nutrient ingredient which chelates with various useful minerals, resulting in inhibiting their uptake and use. Recently, this chelating effect of phytic acid has been used for neutralizing, detoxifying or discharging noxious substance, radiation pollutants or carcinogens. However, there is no attempt to use phytic acid in a cross-linking reaction such as ionic gelation reaction. The present invention uses phytic acid as a cross-linking agent for a cationic biocompatible polymer such as chitosan, and when such a use is applied to the following method of preparing a chitosan capsule according to the present invention, it is possible to more rapidly and stably form a capsule rather than the prior art.

Further, the present invention provides a method of preparing a chitosan capsule, which comprises a first step of preparing an aqueous solution containing chitosan and a soluble active ingredient; a second step of preparing an aqueous solution containing phytic acid; and a third step of bringing the aqueous solution prepared in the first step into contact with the aqueous solution prepared in the second step to perform ionic gelation reaction of chitosan with phytic acid.

Hereinafter, each step of the method of preparing a chitosan capsule in accordance with the present invention will be described in more detail.

In the method of preparing a chitosan capsule according to the present invention, the first step preferably comprises:

(a) preparing a chitosan aqueous solution by adding chitosan to an aqueous solution;

(b) preparing a soluble active ingredient aqueous solution; and (c) mixing the chitosan aqueous solution with the soluble active ingredient aqueous solution.

In step (a), the chitosan aqueous solution preferably comprises a weak acid. At this time, it is preferable to comprise the weak acid at a concentration ranging from 0.01% (w/v) to 20% (w/v), more preferably, 1% (w/v) to 3% (w/v), but is not limited thereto. If the concentration of the weak acid in the chitosan aqueous solution is lower than 0.01% (w/v), it is difficult to dissolve a sufficient amount of chitosan. On the other hand, if it exceeds 20% (w/v), the acidity of the chitosan aqueous solution becomes too high, which has a bad influence on the active ingredient to be encapsulated. There is no limitation on the kind of the weak acid, and there may be used organic acid such as acetic acids, lactic acid, citric acid, formic acid, lactic acid, ascorbic acid, oxalic acid and the like, and inorganic acids such as dilute hydrochloric acid, dilute sulfuric acid and the like. In the present invention, it is more preferable to use acetic acid. In this case, it is preferable to prepare an acetic acid solution with pH 6 or below.

Further, the chitosan aqueous solution of step (a) preferably comprises chitosan at a concentration ranging from 0.01 to 50% (w/v), more preferably, 1 to 5% (w/v). If the concentration of chitosan in the chitosan aqueous solution is lower than 0.01% (w/v), the viscosity of the chitosan aqueous solution is too low and the amount of chitosan is too small to form a capsule, and so it is difficult to create the capsule. In contrast, if it exceeds 50% (w/v), because of too high viscosity of the chitosan aqueous solution, it is difficult to perform an encapsulation process.

The soluble active ingredient aqueous solution of step (b) may be prepared by dissolving an active ingredient in an aqueous phase such as distilled water, and removing bubbles therefrom by settling the resulting solution if necessary. In the soluble active ingredient aqueous solution, the content of a soluble active ingredient is preferably 0.01% (w/v) or more, more preferably, 1% (w/v) or more. If the concentration of the soluble active ingredient in the soluble active ingredient aqueous solution is below 0.01% (w/v), the amount of the active ingredient to be delivered in vivo is too low, so that although the encapsulated active ingredient is taken, there is a possibility that the encapsulated active ingredient does not exert its desired function. However, the above description is nothing but an example of the present invention, and it is possible to modify the content of an active ingredient according to the kind of the active ingredient used in the present invention and the use of a capsule. Accordingly, there is no limitation on the upper limit of the active ingredient's content, but it is preferable to use a saturated solution in which the solution is saturated with the active ingredient. For example, the active ingredient aqueous solution may comprise 3 to 40% (w/v) of a soluble active ingredient.

The mixing of the chitosan aqueous solution with the soluble active ingredient aqueous solution in step (c) is carried out by a conventional mixing means. That is, the soluble active ingredient aqueous solution is added to the chitosan aqueous solution, followed by dispersing the soluble active ingredient by means of a stirrer. Then, if necessary, the resulting solution is left alone for a while so as to remove bubbles.

In the method of preparing a chitosan capsule according to the present invention, the second step is a step of preparing a phytic acid-containing aqueous solution.

The phytic acid aqueous solution of the second step preferably has pH 0.5 to pH 7, more preferably, pH 1 to pH 6, most preferably, pH 1 to pH 2. If the phytic acid aqueous solution has pH below 0.5, its acidity is too strong, resulting in exerting a bad influence on the encapsulated active ingredient. On the other hand, if its pH exceeds 7, there is a problem of lowering an encapsulation yield.

Further, there is no limitation on the content of phytic acid in the phytic acid aqueous solution of the second step, but it is preferably 0.1% (w/v) or more, more preferably, 2% (w/v) or more. At this time, there is no limitation on the upper limit of the phytic acid's content, but it is preferable to use a saturated solution in which the aqueous solution is saturated with phytic acid. More preferably, the content of phytic acid in the phytic acid aqueous solution is 8% (w/v) or below. If the content of phytic acid in the phytic acid aqueous solution is lower than 0.1% (w/v), the cross-linking agent is too small, which occurs the decrease in an encapsulation efficiency of a capsule and stability in a gastric juice. If phytic acid is excessively added rather than its saturation state, the phytic acid solution's acidity is too high, thereby exerting a bad influence on the active ingredient to be encapsulated.

There is no limitation on a method of controlling a concentration and pH of the phytic acid aqueous solution, and it can be achieved by a conventional method well-known in the art. For instance, the phytic acid solution is added to distilled water and stirred to adjust the concentration of phytic acid to water, followed by regulating its pH by using a base such as a 5 N sodium hydroxide solution.

In the method of preparing a chitosan capsule according to the present invention, the third step is a step to perform ionic gelation reaction between chitosan and phytic acid by bringing the aqueous solution prepared in the first step into contact with the aqueous solution prepared in the second step. At this time, there is no limitation on the contact method between the aqueous solutions, and it can be achieved by a conventional method well-known in the art. Examples of the contact method may include a method of mixing the aqueous solution prepared in the first step with the aqueous solution prepared in the second step under stirring; a method of dropping the aqueous solution prepared in the second step to the aqueous solution prepared in the first step; and a method of dropping the aqueous solution prepared in the first step to the aqueous solution prepared in the second step. In terms of efficiency such as reaction time, it is preferable to drop the aqueous solution prepared in the first step to the aqueous solution prepared in the second step. The method of dropping the aqueous solution described above is performed by delivering a certain amount of the aqueous solution to be dropped by means of a metering pump such as a pressure delivery pump, a centrifugal pump, a cascade pump, a hydraulic diaphragm pump, a screw pump and the like, and adding the delivered aqueous solution in a dropping manner by means of a device such as a syringe, an air nozzle, a pressure nozzle, an ultrasonic nozzle, a rotation atomizer and the like. There is no limitation on the gelation reaction, but it is preferable to perform the gelation reaction at a temperature ranging from 0 to 80° C. for 10 seconds to 60 minutes, more preferably, at a temperature ranging from 2 to 40° C. for 1 minute to 30 minutes.

The method of preparing a chitosan capsule according to the present invention may further comprise one or more steps selected from the group consisting of: separating the chitosan capsule prepared in the third step, washing and drying the same.

The separation of chitosan capsule may be carried out by using a conventional method in the art such as filtration and the like, the washing thereof may be performed by using distilled water and the like, and the drying thereof may be also conducted by using a conventional drying mean, preferably, freeze drying.

In an embodiment, a chitosan capsule of the present invention may be prepared as follows. Chitosan used as a main ingredient of a capsule is dissolved in an 1% acetic acid aqueous solution to prepare a chitosan solution. A soluble active ingredient is dissolved in an aqueous solution such as distilled water to prepare a soluble active ingredient aqueous solution. The prepared two aqueous solutions are mixed under stirring to prepare a chitosan-soluble active ingredient solution, followed by adding the same to the phytic acid aqueous solution drop by drop to prepare a capsule. At this time, the capsule is shaped by forming a film on the surface of a droplet of the chitosan-soluble active ingredient solution falling into the cross-linking agent solution while binding multivalent cations of chitosan to multivalent anions of phytic acid. Further, the phytic acid particles having high diffusivity penetrate into the capsule and bind to the chitosan molecules in the inside of the capsule as well as at the surface thereof, resulting in forming a very hard, stable and insoluble capsule. The prepared capsules are separated from the aqueous solution, and washed and dried by using a freeze-drying method and the like, to thereby obtain spherical shaped capsules. Each step of the aforementioned method will be illustrated in FIG. 1.

In the method of the present invention, it is preferable to use a method of adding the mixed solution of chitosan and soluble active ingredient to the phytic acid aqueous solution in a dropping manner, but it is also possible to use a method of mixing the soluble active ingredient with the phytic acid aqueous solution as a cross-linking agent and then adding the resulting solution to the chitosan aqueous solution in a dropping manner. However, in the latter case, since the molecular weight of chitosan is generally larger than that of phytic acid and chitosan is diffused into the mixture of phytic acid and soluble active ingredient, it takes a long time to perform a cross-linking reaction with phytic acid. Thus, there is a problem in that an encapsulation yield is lowered than the method of adding the aqueous solution prepared in the first step to the aqueous solution prepared in the second step in a dropping manner.

Further, the present invention relates a pharmaceutical composition comprising the chitosan capsule of the present invention and a pharmaceutically acceptable carrier.

At this time, there is no limitation on the kind of the used carrier, and it is possible to use unrestrictedly carriers and vehicles conventionally used in the medicinal field. Examples of the carriers may include ion exchange resin, alumina, aluminum stearate, lecithin, serum proteins (e.g., human serum albumin), buffering materials (e.g., various kinds of phosphates, glycine, sorbic acid, potassium sorbate, partially glyceride mixture of saturated vegetable fatty acid), water, salts or electrolytes (e.g., protamine sulfate, disodium hydrogen phosphate, potassium hydrogen phosphate, sodium chloride and zinc salt), collagenic silica, magnesium trisilicate, polyvinyl pyrrolidone, cellulose-based substrates, polyethylene glycol, sodium carboxymethylcellulose, polyarylate, wax, polyethylene glycol, lanolin and the like, but are not limited thereto. The pharmaceutical composition of the present invention may further comprise lubricants, humectants, emulsifying agents, suspension agents, preservatives, and the like besides the aforementioned ingredients. The pharmaceutical composition of the present invention may be prepared using the chitosan capsule of the present invention and a pharmaceutically acceptable carrier by a conventional method well-known in the art, and there is no limitation on the method.

In addition, the present invention provides a food composition comprising the chitosan capsule of the present invention and a food additive.

The food composition of the present invention may include functional foods such as health supplementary foods and health foods, and further comprise food additives such as sitologically acceptable carriers, excipients and/or diluents. Examples of the aforementioned carriers, excipients and/or diluents may include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methyl hydroxy benzoate, propyl hydroxy benzoate, talc, magnesium stearate, mineral oil and the like, but are not limited thereto. The food composition of the present invention may be prepared by using the chitosan capsule of the present invention and the food additive by a conventional method well-known in the art.

The present invention provides a cosmetic composition comprising the chitosan capsule of the present invention and a cosmetic additive.

Examples of the cosmetic additive may include emulsifying agents; thickening agents such as metal silicate, xanthan gum, cellulose and carbomer; an aqueous phase such as distilled water, propylene glycol, 1,3-butylene glycol, glycerin, betaine or sorbitol; preservatives; perfumes; and dyes, but are not limited thereto. The cosmetic composition of the present invention may be prepared by using the chitosan capsule of the present invention and the cosmetic additive by a conventional method well-known in the art.

Hereinafter, the present invention will now be described in detail with reference to the following examples. The examples are only for illustrative purposes, and the present invention is not limited thereto.

Preparative Example 1

Preparation of Chitosan Solution

Chitosan was added to an acetic acid solution having an acidity of 1% (v/v) so that its final concentration becomes 3% (w/v), and the mixture was stirred at 300 rpm for 10 minutes using a magnetic stirrer, thereby obtaining a chitosan solution. At this time, chitosan used as a biodegradable polymer has an average molecular weight of 85,000 daltons, and shows a viscosity of about 5.6 cps and a deacetylation rate of about 98% when dissolved in a 0.5% (w/v) acetic acid solution so that its concentration becomes 0.5% (w/v).

Preparative Example 2

Preparation of Bovine Serum Albumin-Chitosan Aqueous Solution

Bovine serum albumin (Sigma-Aldrich) as a soluble active ingredient was dissolved in the deionized water to have a concentration of 15% (w/v). The aqueous solution was added to the chitosan aqueous solution prepared in Preparative Example 1, stirred at 500 rpm for 10 minutes using a magnetic stirrer to disperse bovine serum albumin, and then, left alone for a while to remove bubbles from the chitosan solution, to thereby obtain a bovine serum albumin-chitosan aqueous solution.

Example 1

Preparation of Chitosan-Phytic Acid Capsule Comprising Bovine Serum Albumin

Phytic acid aqueous solutions were adjusted to 3, 4 and 5% in concentration, respectively, and each aqueous solution was differently adjusted to have pH 1, pH 2, pH 4 and pH 6, thereby preparing capsules. Specifically, the phytic acid solution was added to distilled water and stirred to regulate the concentration of phytic acid to water, followed by regulating its pH by using a 5.0 N sodium hydroxide solution. The bovine serum albumin-chitosan aqueous solution prepared in Preparative Example 2 was added to the resulting solution drop by drop using a metering pump, and the resulting mixture was reacted for 30 minutes to induce the binding between chitosan and phytic acid, thereby preparing the capsules. The prepared capsules were separated from the mixture, washed with distilled water two or three times, and then dried by a freeze-dry method. At this time, an initial freezing process was performed at −40° C. for 4 hours, followed by drying the capsules at −30° C. for 3 hours, −10° C. for 2 hours, 0° C. for 1 hour, 20° C. for 2 hours, and 30° C. for 5 hours.

Experimental Example 1

Bovine Serum Albumin Encapsulation Efficiency of Chitosan-Phytic Acid Capsule

Figure 2:
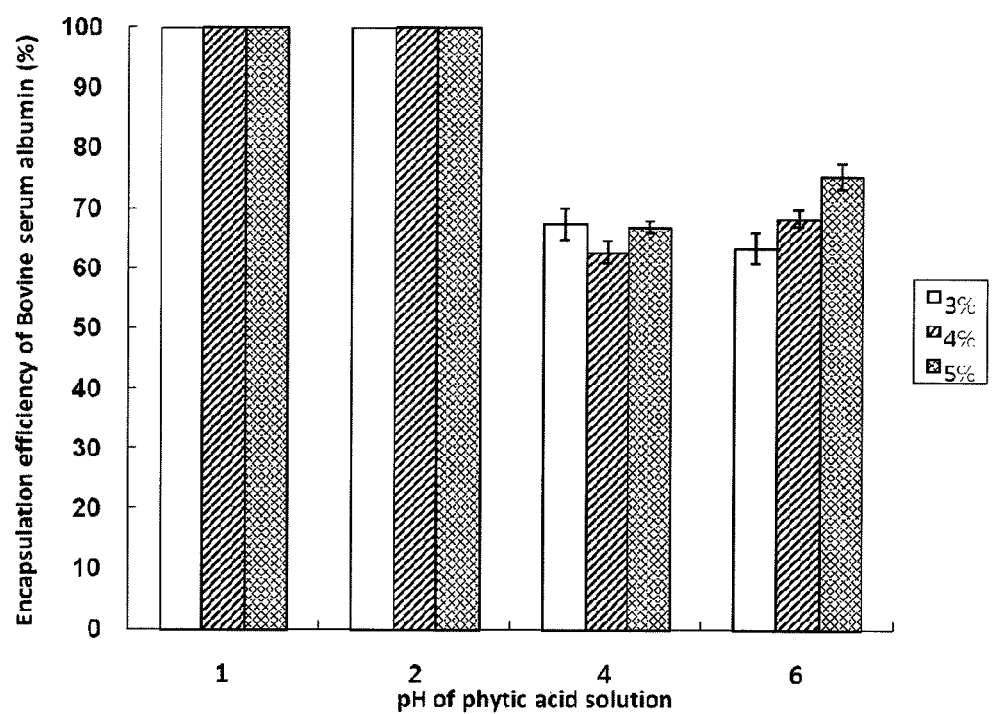
FIG. 2 is a graph showing a bovine serum albumin encapsulation efficiency depending on a concentration and pH of phytic acid in a chitosan-phytic acid capsule prepared according to Example 1.

In order to measure the influence of a concentration and pH of phytic acid on the degree of encapsulation, a bovine serum albumin encapsulation efficiency of each capsule prepared in Example 1 was calculated. The amount of unencapsulated albumin remaining in the phytic acid solution after capsule formation was measured by a Bradford's method, and a bovine serum albumin encapsulation efficiency of the capsule was calculated by using the data. The results are shown in FIG. 2. As shown in FIG. 2, when the phytic acid solution had pH 1 and pH 2, the capsule exhibited an encapsulation efficiency of 100% regardless of the concentration of phytic acid, and in case of pH 4 and pH 6, the capsule exhibited an encapsulation efficiency of 60 to 80% depending on the concentration of phytic acid.

Experimental Example 2

Figure 3:
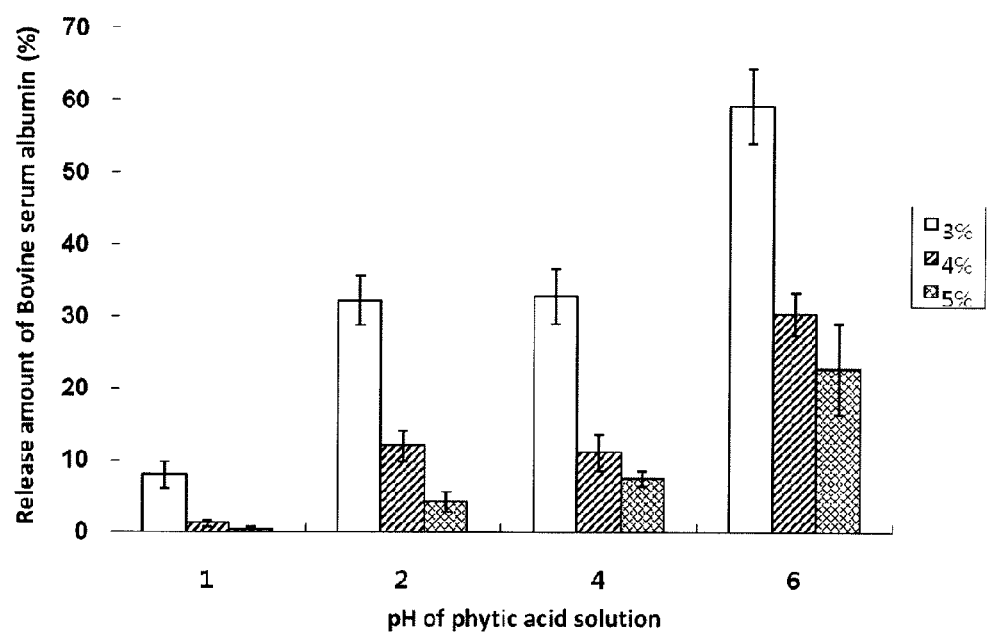
FIG. 3 is a graph showing the release amount of bovine serum albumin depending on a concentration and pH of phytic acid when the chitosan-phytic acid capsule prepared according to Example 1 is treated with an artificial gastric juice.

Stability of Chitosan-Phytic Acid Capsule Comprising Bovine Serum Albumin in Artificial Gastric Juice Each capsule prepared in Example 1 was put into an artificial gastric juice (HCl 0.7% (v/v), NaCl 0.2% (w/v) in water) with pH 1.2 and shaken at 100 rpm for 2 hours in a 37° C. shaking incubator. Thereafter, the amount of bovine serum albumin released into the artificial gastric juice was measured by a Bradford's method. Using the data, after the treatment with the artificial gastric juice for 2 hours, the release amount of bovine serum albumin thereinto was calculated, and the results are shown in FIG. 3. As shown in FIG. 3, when the phytic acid solution had pH 1 or pH 2, the release amount of bovine serum albumin (0~30%) was lowest after 2 hours, and the higher the concentration of phytic acid was, the lower the release amount of bovine serum albumin was. From these results, it has been confirmed that the chitosan-phytic acid capsule prepared using the phytic acid solution having a high acidity (pH 1~2) and a high concentration of phytic acid (5%) is more stable under acidic conditions such as the gastric juice.

Example 2

Preparation of Chitosan-Phytic Acid Capsule Comprising Bovine Serum Albumin

The chitosan solution prepared by the same method as described in Preparative Example 1 was mixed with the bovine serum albumin solution prepared by the same method as described in the Preparative Example 2 at a weight ratio of 9:1, and the resulting mixture was stirred at 100 rpm for 10 minutes by using a stirrer, to thereby prepare a chitosan solution comprising bovine serum albumin. A 58% (w/w) phytic acid solution was added to distilled water so that the final concentration of phytic acid becomes 5% (w/w), and its pH was adjusted to pH 1 using a 5 N NaOH solution, to thereby prepare a phytic acid solution. The prepared bovine serum albumin-chitosan solution was delivered to a syringe by means of a pressure delivery pump and added to the prepared phytic acid solution in a dropping manner, thereby forming spherical capsules through the binding between chitosan and phytic acid. The capsules were separated from the remaining phytic acid solution through filtration. The separated capsules were washed with distilled water to remove phytic acid remaining at the surface thereof, and subjected to freeze-drying, thereby forming the capsules according to the present invention.

Comparative Example 1

Preparation of Chitosan-Tripolyphosphate Capsule Comprising Bovine Serum Albumin After a chitosan capsule was prepared using tripolyphosphate which has been widely used as a cross-linking agent for preparing a chitosan capsule, its encapsulation efficiency for a soluble active ingredient and stability thereof in a gastric juice were measured and compared with those of the chitosan-phytic acid capsule prepared according to the present invention. First, a bovine serum albumin-chitosan solution was prepared by the same method as described in Example 2. In order to choose a concentration and pH of tripolyphosphate suitable for preparing a capsule, tripolyphosphate aqueous solutions were adjusted to have concentrations of 2% (w/v), 4% (w/v) and 6% (w/v), and each aqueous solution was adjusted to have pH 3, pH 5 and pH 7. A chitosan-tripolyphosphate capsule was prepared by the same method as described in Example 2.

Comparative Experimental Example 1

Figure 4:
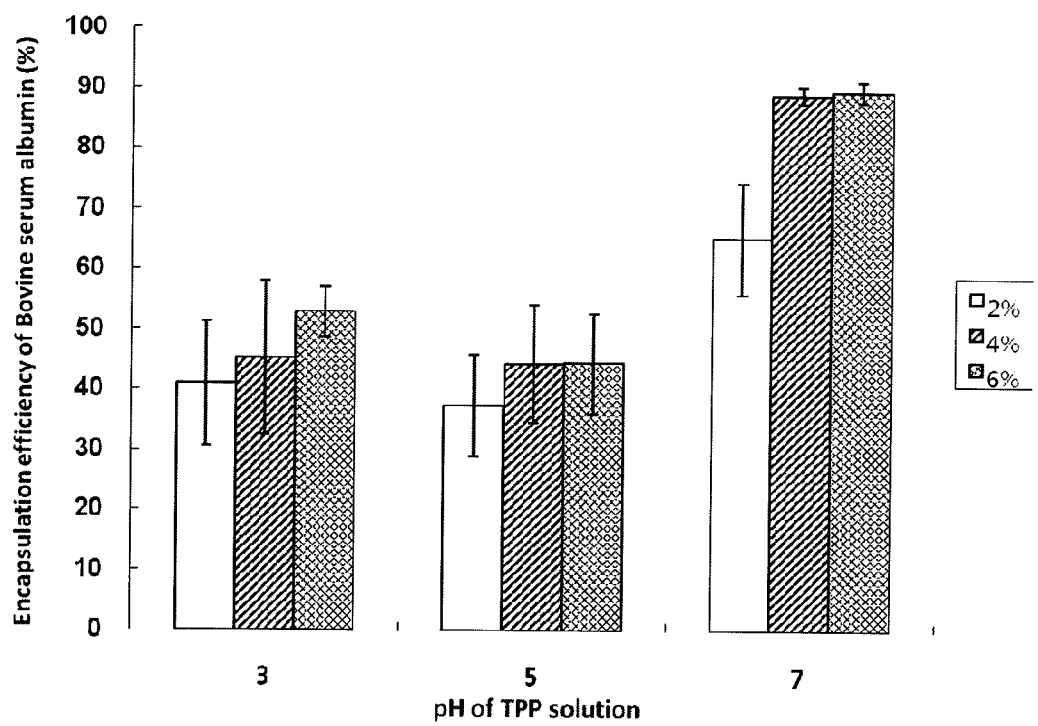
FIG. 4 is a graph showing a bovine serum albumin encapsulation efficiency depending on a concentration and pH of tripolyphosphate in a chitosan-tripolyphosphate capsule prepared according to Comparative Example 1.

Bovine Serum Albumin Encapsulation Efficiency of Chitosan-Tripolyphosphate Capsule A bovine serum albumin encapsulation efficiency of the chitosan-tripolyphosphate capsule prepared in Comparative Example was measured by the same method as described in Experimental Example 1, and the results are shown in FIG. 4. As shown in FIG. 4, the chitosan-tripolyphosphate capsule of Comparative Example 1 exhibited the highest encapsulation efficiency when its pH was 7 and its tripolyphosphate concentration was 4% (w/v) and 6% (w/v), but it was only 85%, which was lower than that of the example according to the present invention.

Comparative Experimental Example 2

Figure 5:
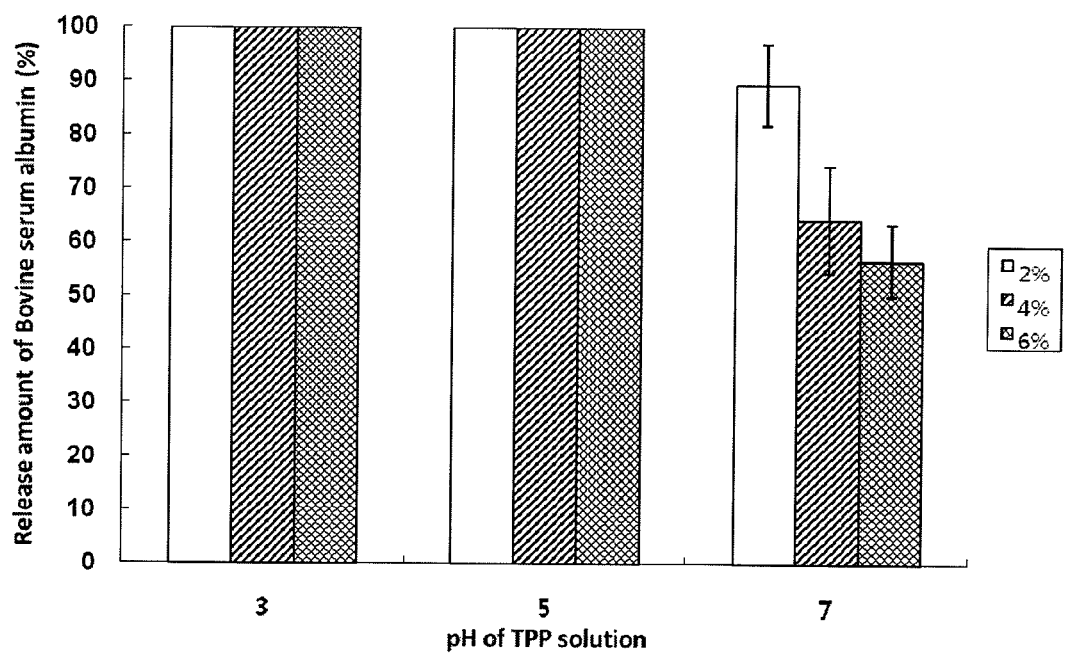
FIG. 5 is a graph showing the release amount of bovine serum albumin depending on a concentration and pH of tripolyphosphate when the chitosan-tripolyphosphate capsule prepared according to Comparative Example 1 is treated with an artificial gastric juice.

Stability of Chitosan-Tripolyphosphate Capsule Comprising Bovine Serum Albumin in Artificial Gastric Juice The stability of the chitosan-tripolyphosphate capsule prepared in Comparative Example 1 in an artificial gastric juice was measured by the same method as described in Experimental Example 2, and the results are shown in FIG. 5. As shown in FIG. 5, in the chitosan-tripolyphosphate capsule prepared in the comparative example, the most stable pH thereof in the artificial gastric juice was pH 7. Further, even if the concentration of tripolyphosphate was 6% (w/v), 55% or more of bovine serum albumin was released into the artificial gastric juice, and 45% or below thereof only remaining within the capsule. Therefore, it has been confirmed that the binding affinity between chitosan and tripolyphosphate is weaker than that between chitosan and phytic acid, and such a binding is easy to break under strong acid conditions of the gastric juice, thereby deteriorating the protection effect of the capsule for the encapsulated soluble active ingredient.

Experimental Example 3

Figure 6:
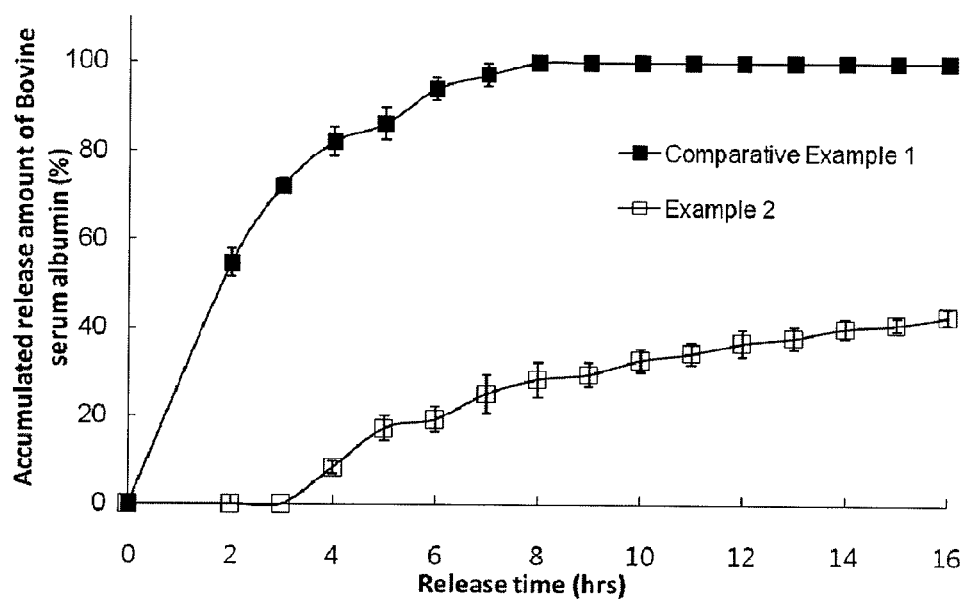
FIG. 6 is a graph showing the accumulated release amount of bovine serum albumin depending on time when a chitosan-phytic acid capsule prepared according to Example 2 and the chitosan-tripolyphosphate capsule prepared according to Comparative Example 1 are treated with artificial gastric and intestinal juices.

Measurement of Sustained-Release of Bovine Serum Albumin in Intestine for Chitosan-Phytic Acid Capsule and Chitosan-Tripolyphosphate Capsule In case of the encapsulated soluble active ingredient being absorbed through the intestinal wall, if the external wall of the capsule does not break down in the intestine, bioavailability of the soluble active ingredient encapsulated inside the capsule is deteriorated. Thus, in order to examine the bioavailability of the prepared capsule, an artificial gastric juice (pH 1.2) and an artificial intestinal juice (0.2 M $KH_2PO_4$ 25% (v/v), 0.2 N NaOH 11.8% (v/v) in water, pH 6.8) were prepared. Then, the release amount of bovine serum albumin from the chitosan-phytic acid capsule prepared in Example 2 according to the present invention and the chitosan-tripolyphosphate capsule prepared by using the solution with pH 7 and a tripolyphosphate concentration of 6% (w/v) in Comparative Example 1 were measured. A bovine serum albumin encapsulation efficiency of each prepared capsule was measured by the same method as described in Experimental Example 1. As a result, the chitosan-phytic acid capsule prepared according to the present invention exhibited 100% encapsulation efficiency for the soluble active ingredient. When the capsule was put in the artificial gastric juice identical to that of Experimental Example 2 and shaken at 100 rpm for 2 hours in a 37° C. shaking incubator, it showed 20% or below of the amount of the encapsulated soluble active ingredient is released. On the other hand, the chitosan-tripolyphosphate capsule showed 50% or more of the amount of bovine serum albumin is released under the same conditions. When the capsule shaken in the artificial gastric juice was put in the artificial intestinal juice and shaken at 37° C., 100 rpm, as shown in FIG. 6, the accumulated amount of the soluble active ingredient released from the chitosan-phytic acid capsule was 10% after 4 hours and 40% after 10 hours, which means that the soluble active ingredient is gradually released. However, in case of the chitosan-tripolyphosphate capsule, it showed 100% accumulated release amount of bovine serum albumin within 4 hours. It could be seen from these results that the capsule prepared according to the present invention exhibited a pH-dependent sustained-release property. From these results, it can be expected that 80% or more of the encapsulated soluble active ingredient is released from the chitosan-phytic acid capsule and absorbed in the intestine, while 50% or below of the encapsulated soluble active ingredient is released from the chitosan-tripolyphosphate capsule and absorbed in the intestine.

Experimental Example 4

Figure 7:
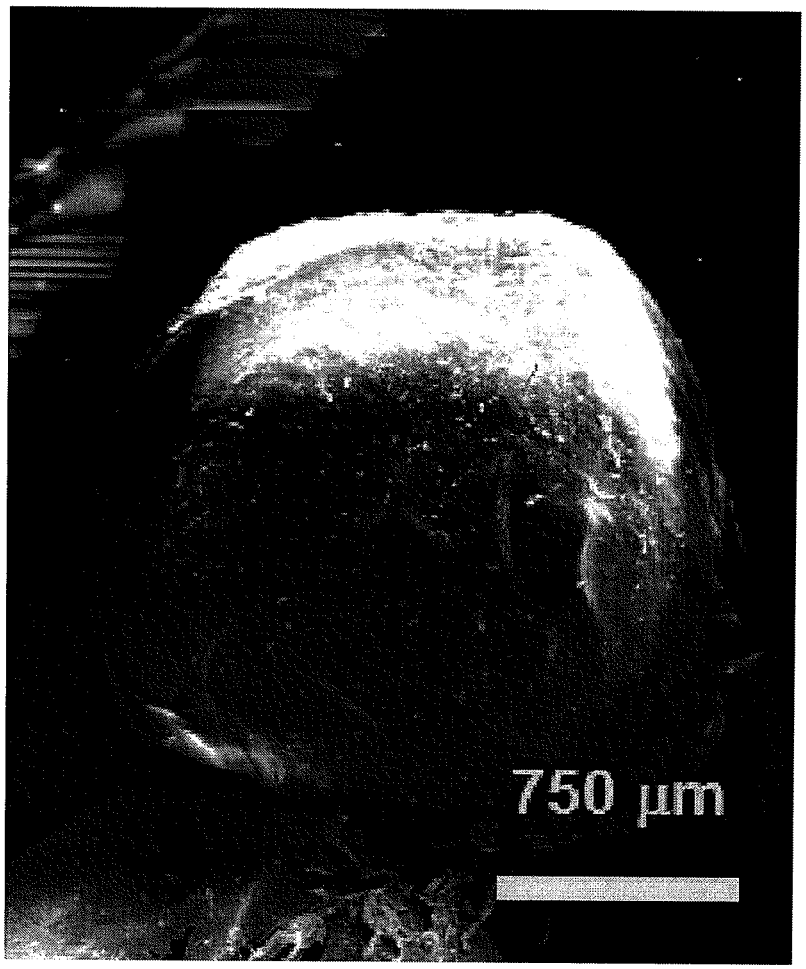
FIG. 7 is a scanning electron microscope (SEM) photograph of the capsule prepared according to Example 2.
Figure 8:
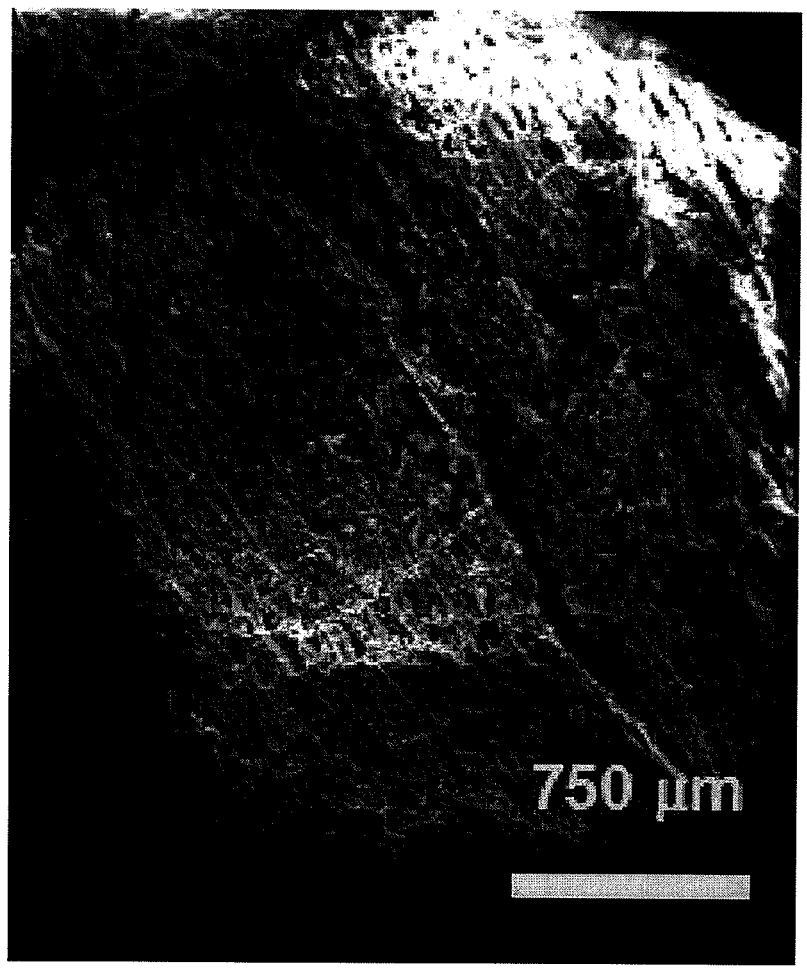
FIG. 8 is an SEM photograph of the capsule prepared according to Comparative Example 1.
Figure 9:
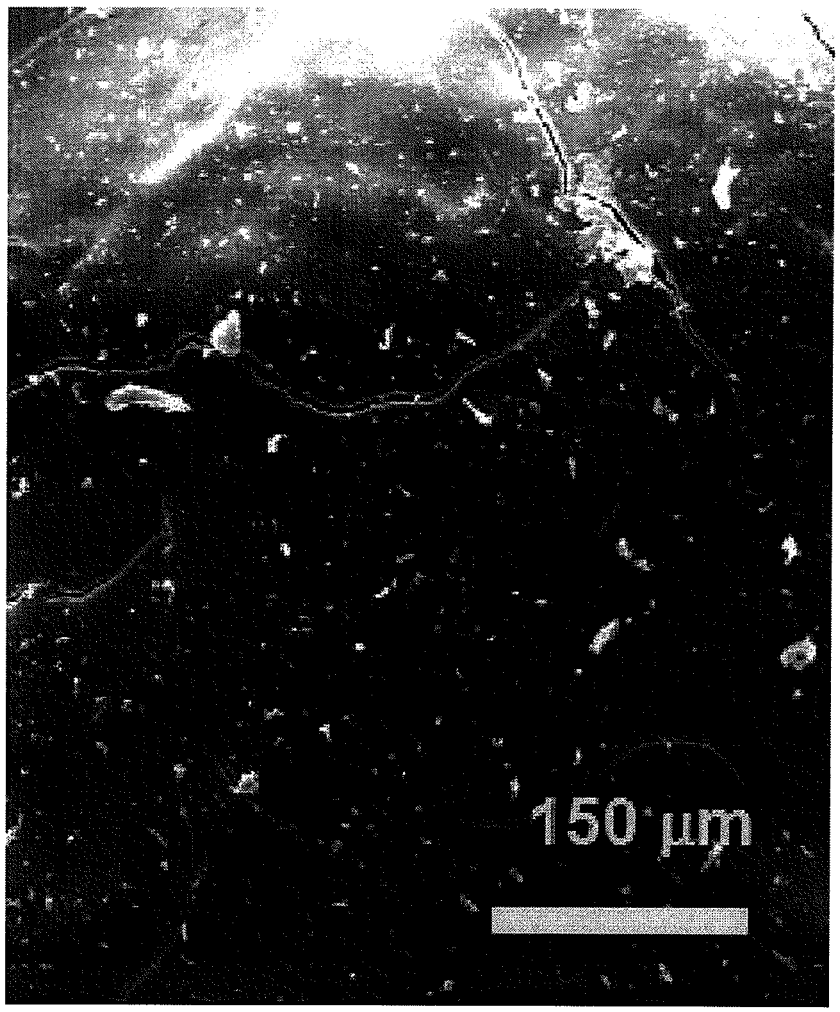
FIG. 9 is an SEM photograph in which the photograph of FIG. 7 is magnified ten times.
Figure 10:
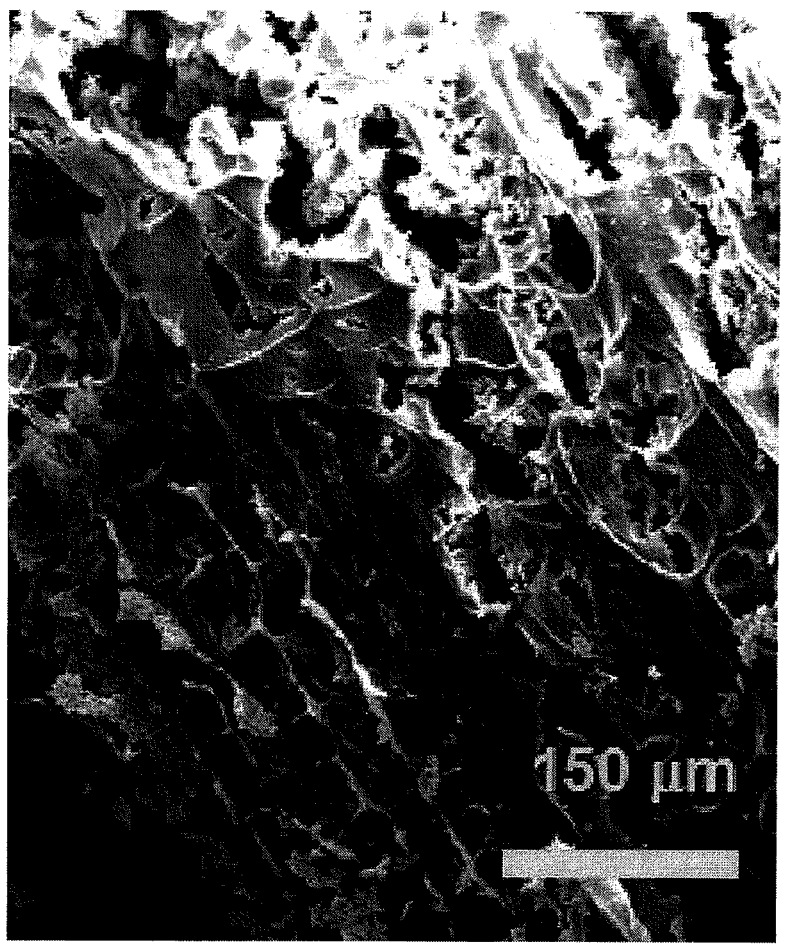
FIG. 10 is an SEM photograph in which the photograph of FIG. 8 is magnified ten times.

Photographic Analysis of Surfaces of Chitosan-Phytic Acid Capsule and Chitosan-Tripolyphosphate Capsule Surfaces of the chitosan-phytic acid capsule prepared in Example 2 and the chitosan-tripolyphosphate capsule prepared using the solution with pH 7 and a tripolyphosphate concentration of 6% (w/v) in Comparative Example 1 were photographed using an electron microscope and shown in FIGS. 7 and 8. As shown in FIGS. 7 and 8, it was observed with an electron microscope that both the capsules have a relatively spherical shape. However, the capsule of Example 2 exhibited a more stable shape where its surface was smooth and firm as shown in FIG. 7, whereas the chitosan-tripolyphosphate capsule of Comparative Example 1 had a very coarse and creviced surface as shown in FIG. 8. Such a difference was more distinguished when observed under higher magnifications (see FIGS. 9 and 10). These results showed that phytic acid more strongly binds to chitosan to form a smooth film surface having a few crevices, which results in improving the protection effect of the capsule for the soluble active ingredient under acidic conditions.

Preparative Example 3

Preparation of Insulin-Chitosan Aqueous Solution

Insulin (Sigma-Aldrich) as a soluble active ingredient was dissolved in a 0.1 N HCl solution to have final concentrations of 3% (w/v), 5% (w/v), 10% (w/v) and 15% (w/v). Each insulin solution was added to the chitosan aqueous solution prepared in Preparative Example 1, stirred at 500 rpm for 10 minutes using a magnetic stirrer to disperse insulin, and then, left alone for a while to remove bubbles from the chitosan solution, to thereby obtain an insulin-chitosan aqueous solution.

Example 3

Preparation of Chitosan-Phytic Acid Capsule Comprising Insulin

The phytic acid aqueous solution at a concentration of 5% was prepared, and its pH was adjusted to 1, thereby preparing the capsule. Specifically, the phytic acid solution was added to distilled water and stirred to regulate the concentration of phytic acid to water, followed by regulating its pH using a 2.0 N sodium hydroxide solution. The insulin-chitosan solution prepared in Preparative Example 3 was added to the resulting solution drop by drop using a metering pump, and the resulting mixture was reacted to induce the binding between chitosan and phytic acid, thereby preparing the capsule. The prepared capsules were separated from the mixture, washed with distilled water two or three times, and then dried by a freeze-dry method. At this time, an initial freezing process was performed at −40° C. for 4 hours, followed by drying the capsules at −30° C. for 3 hours, −10° C. for 2 hours, 0° C. for 1 hour, 20° C. for 2 hours, and 30° C. for 5 hours.

Experimental Example 5

Insulin Encapsulation Efficiency of Chitosan-Phytic Acid Capsule

In order to measure the degree of encapsulation according to an insulin concentration, an insulin encapsulation efficiency of each capsule prepared in Example 3 was calculated. The amount of unencapsulated insulin in the phytic acid solution remaining after the capsule formation was measured using HPLC, and an insulin encapsulation efficiency of the capsule was calculated by using the data. The results are shown in FIG. 11. As shown in FIG. 11, when the phytic acid solution has pH 1, the lower the concentration of insulin was, the higher the encapsulation efficiency was. In particular, in a case where the concentration of insulin was 3%, 100% of an encapsulation efficiency was exhibited.

Comparative Example 2

Preparation of Chitosan-Tripolyphosphate Capsule Comprising Insulin

After a chitosan capsule was prepared using tripolyphosphate which has been widely used as a cross-linking agent for preparing a chitosan capsule, its encapsulation efficiency for a soluble active ingredient and stability thereof in the gastric juice were measured and compared with the chitosan-phytic acid capsule prepared according to the present invention. First, an insulin solution was prepared to have an insulin concentration of 3% (w/v) in Preparative Example 3, and an insulin-chitosan solution was prepared by the same method as described in Preparative Example 3. In order to select a concentration and pH of tripolyphosphate suitable for preparing a capsule, tripolyphosphate aqueous solutions were adjusted to have concentrations of 4% (w/v), 5% (w/v), 6% (w/v) and 7% (w/v), respectively, and each aqueous solution was adjusted to have pH 3, pH 5 and pH 7. The capsule was prepared by the same method as described in Example 3.

Comparative Experimental Example 3

Insulin Encapsulation Efficiency of Chitosan-Tripolyphosphate Capsule

An insulin encapsulation efficiency of the chitosan-tripolyphosphate capsule prepared in Comparative Example 2 was measured by the same method as described in Experimental Example 5, and the results are shown in FIG. 12. As shown in FIG. 12, in case of the chitosan capsule of the comparative example, when the concentration of tripolyphosphate was 4% or more, the insulin encapsulation efficiency was not significantly influenced by the concentration of tripolyphosphate, and the change in pH of the tripolyphosphate aqueous solution had a significant influence on the insulin encapsulation efficiency. The chitosan-tripolyphosphate capsule exhibited the highest encapsulation efficiency when pH 7 and tripolyphosphate concentrations of 4% (w/v), 5% (w/v) and 6% (w/v), but it was about 90%, which was lower than that of the example of the present invention.

Example 4

Preparation of Chitosan-Phytic Acid Capsule Comprising Insulin

In order to measure the degree of insulin encapsulation according to a concentration and pH of phytic acid used as a cross-linking agent, a chitosan solution comprising insulin was prepared according to a method of showing the highest insulin encapsulation efficiency among the insulin-chitosan aqueous solutions of Preparative Example 3. That is, the insulin aqueous solution having an insulin concentration of 3% (w/v) and the chitosan solution prepared by the same method as described in Preparative Example 1 were mixed so that a weight ratio of chitosan solution to insulin solution was 9:1 and stirred at 100 rpm for 10 minutes by means of a stirrer, thereby preparing a chitosan solution comprising insulin. A 58% (w/w) phytic acid solution was diluted with distilled water to have phytic acid concentrations of 4% (w/w), 5% (w/w), 6% (w/w) and 7% (w/w), and each solution was adjusted to have pH 1, pH 2, pH 4 and pH 6 using a 5 N NaOH solution, thereby preparing a phytic acid solution. The prepared insulin-chitosan solution was delivered to a syringe by means of a pressure delivery pump and added to the prepared phytic acid solution in a dropping manner, thereby forming spherical capsules through the binding between chitosan and phytic acid. The capsules were separated from the remaining phytic acid solution through filtration. The separated capsules were washed with distilled water to remove phytic acid remaining at the surface thereof, and subjected to freeze-drying, thereby forming the capsules according to the present invention.

Experimental Example 6

Figure 13:
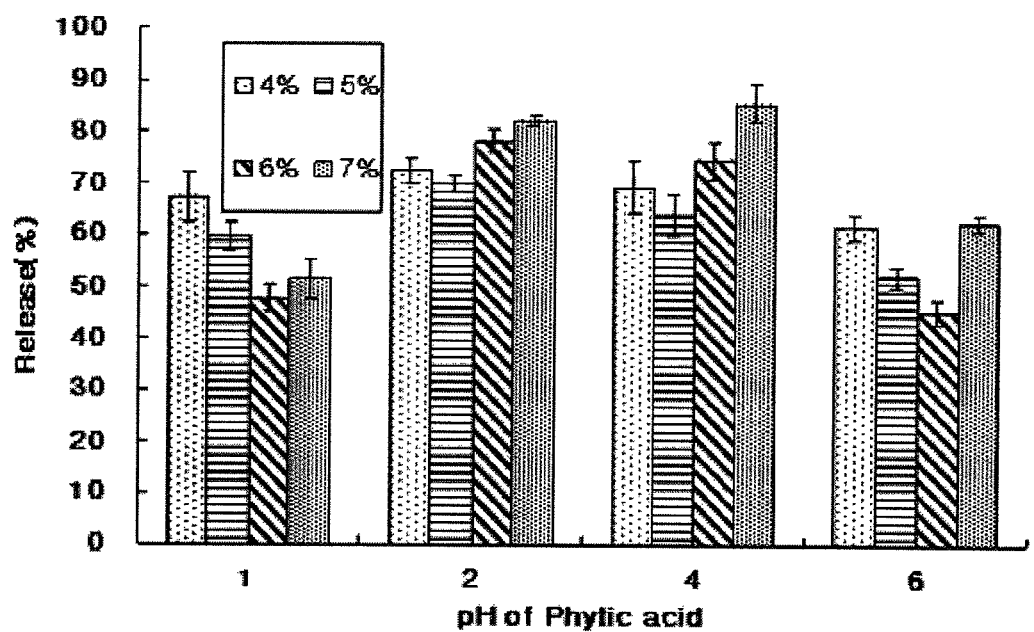
FIG. 13 is a graph showing the release amount of insulin depending on a concentration and pH of phytic acid when a chitosan-phytic acid capsule prepared according to Example 4 is treated with an artificial gastric juice.

Stability of Chitosan-Phytic Acid Capsule Comprising Insulin in Artificial Gastric Juice Each capsule prepared in Example 4 was put into an artificial gastric juice (HCl 0.7% (v/v), NaCl 0.2% (w/v) in water) with pH 1.2 and shaken at 100 rpm for 2 hours in a 37° C. shaking incubator. Thereafter, the amount of insulin released into the artificial gastric juice was measured by HPLC. Using the data, after the treatment with the artificial gastric juice for 2 hours, the release amount of insulin thereinto was calculated, and the results are shown in FIG. 13. As shown in FIG. 13, it could be seen that when the phytic acid solution had pH 1 or pH 6, the release amount of insulin (40~70%) was lowest after 2 hours, and when the concentration of phytic acid was 6%, the release amount of insulin was lowest. From these results, it has been confirmed that the chitosan-phytic acid capsule prepared using the phytic acid solution having a high concentration of phytic acid (6%) under acidic (pH 1) and weak acidic (pH 6) conditions is more stable under acidic conditions such as the gastric juice.

Comparative Experimental Example 4

Figure 14:
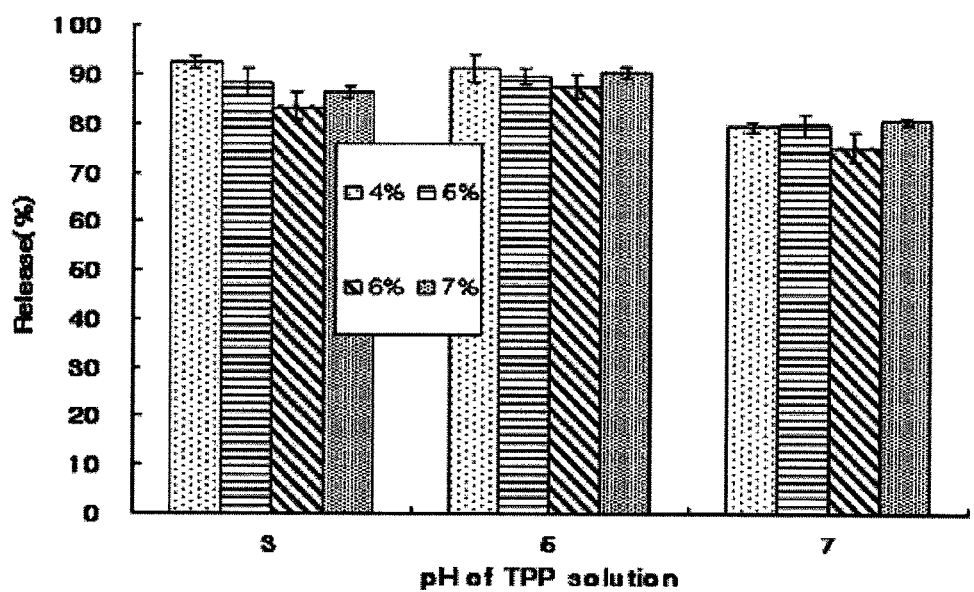
FIG. 14 is a graph showing the release amount of insulin depending on a concentration and pH of tripolyphosphate when the chitosan-tripolyphosphate capsule prepared according to Comparative Example 2 is treated with an artificial gastric juice.

Stability of Chitosan-Tripolyphosphate Capsule Comprising Insulin in Artificial Gastric Juice The stability of the chitosan-tripolyphosphate capsule prepared in Comparative Example 2 in an artificial gastric juice was measured by the same method as described in Experimental Example 6, and the results are shown in FIG. 14. As shown in FIG. 14, in the chitosan-tripolyphosphate capsule prepared in the comparative example, 80% or more insulin was released into the artificial gastric juice regardless of a concentration and pH of tripolyphosphate. Therefore, it has been confirmed that the binding affinity between chitosan and tripolyphosphate is weaker than that between chitosan and phytic acid, and such a binding is easy to break down under strong acid conditions of the gastric juice, thereby deteriorating the protection effect of the capsule for the encapsulated soluble active ingredient.

Experimental Example 7

Figure 15:
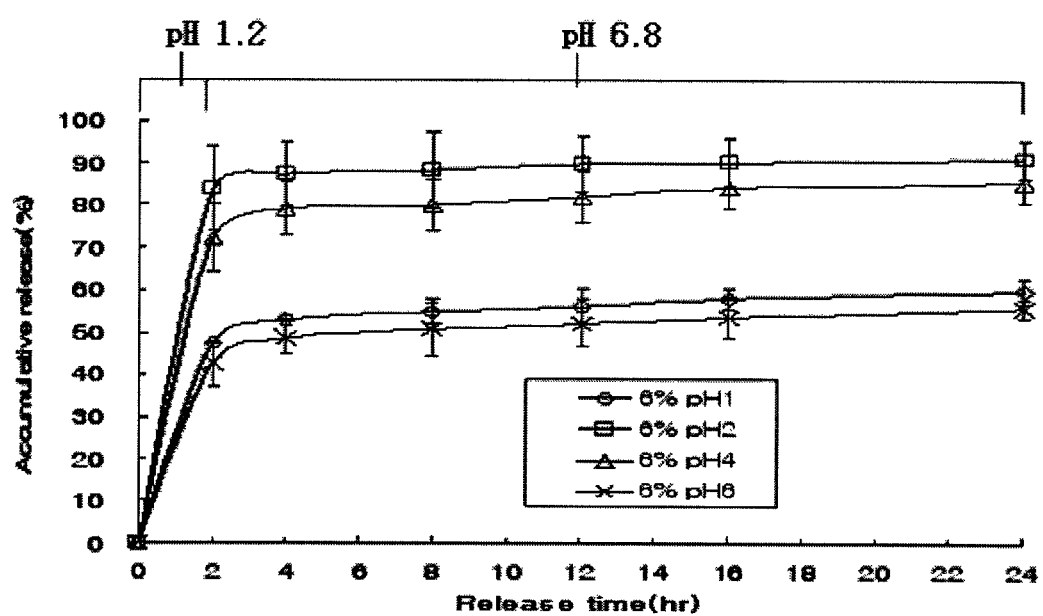
FIG. 15 is a graph showing a release amount of insulin depending on time for 24 hours when four kinds of chitosan-phytic acid capsules prepared by using a 6% phytic acid solution with pH 1, pH 2, pH 4 and pH 6, respectively, according to Example 4 are treated with artificial gastric and intestinal juices.

Measurement of Sustained-Release of Insulin from Chitosan-Phytic Acid Capsule into Intestine In case of the encapsulated soluble active ingredient being absorbed through the intestinal wall, if the external wall of the capsule does not break down in the intestine, bioavailability of the soluble active ingredient encapsulated inside the capsule is deteriorated. Thus, in order to examine the bioavailability of the prepared capsule, an artificial gastric juice (pH 1.2) and an artificial intestinal juice (0.2 M $KH_2PO_4$ 25% (v/v), 0.2 N NaOH 11.8% (v/v) in water, pH 6.8) were prepared. Then, four kinds of the chitosan-phytic acid capsules respectively prepared using a 6% phytic acid solution with pH 1, pH 2, pH 4 and pH 6 in Example 4 were successively treated with the artificial gastric juice and the intestinal juice, and the release amount of insulin from each capsule was measured. The amount of insulin released from the capsule was measured by HPLC, and represented as a percentage (%) with respect to the amount of insulin encapsulated inside the capsule. These results are shown in FIG. 15. When the capsule was put in the artificial gastric juice identical to that of Experimental Example 6 and shaken at 100 rpm for 2 hours in a 37° C. shaking incubator, the release amount of the encapsulated insulin ranging from 40 to 85% was shown. When the capsule treated with the artificial gastric juice was put in the artificial intestinal juice and shaken at 37° C., 100 rpm, as shown in FIG. 15, it has been found that insulin is gradually released from the chitosan-phytic acid capsule. The chitosan-phytic acid capsule, which was most stable under acidic conditions in Experimental Example 6, i.e., prepared using the phytic acid solution with pH 1 and pH 6, exhibited the most preferable result in the above experiment. However, it has been also confirmed that in case of preparing the chitosan-phytic acid capsule using the phytic acid solution with pH 2 or pH 4, insulin is gradually released from the capsule into the artificial intestinal juice. It could be seen from these results that the capsule prepared according to the present invention exhibited a pH-dependent sustained-release effect. From these results, it can be expected that 55% or more of the encapsulated soluble active ingredient is released from the chitosan-phytic acid capsule and absorbed in the intestine.

Comparative Experimental Example 5

Figure 16:
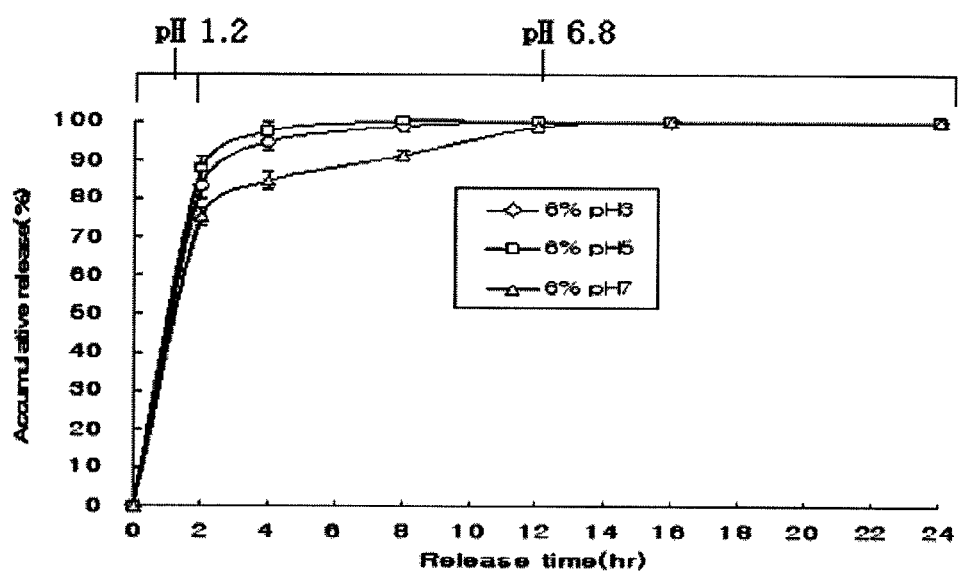
FIG. 16 is a graph showing a release amount of insulin depending on time when chitosan-tripolyphosphate capsules prepared by using a 6% tripolyphosphate solution with pH 3, pH 5 and pH 7, respectively, according to Comparative Example 2 are treated with artificial gastric and intestinal juices.

Measurement of Controlled Release of Insulin from Chitosan-Tripolyphosphate Capsule in Intestine In order to compare bioavailability of the capsule prepared according to the present invention with that of the capsule prepared using a conventional cross-linking agent, the capsules prepared in Comparative Example 2 under the conditions of the tripolyphosphate concentration of 6% and the acidity of pH 3, pH 5 and pH 7 were subjected to the same experiment as described in Experimental Example 7. The release amount of insulin from the capsule was measured according to Experimental Example 7. When the capsules were put in the artificial gastric juice identical to that of Experimental Example 6 and shaken at 100 rpm for 2 hours in a 37° C. shaking incubator, in all kinds of the capsules prepared according to Comparative Example 2, 75% or more of the encapsulated soluble active ingredient was released. When the capsules put in the artificial gastric juice and shaken were put in the artificial intestinal juice and shaken at 37° C., 100 rpm. As shown in FIG. 16, the soluble active ingredient is completely released from the chitosan-tripolyphosphate capsule within 12 hours. In the chitosan-tripolyphosphate capsule, which was most stable under neutral conditions in Comparative Experimental Example 4, i.e., prepared using the tripolyphosphate solution with pH 7, 70% or more of insulin was released into the artificial gastric juice, and then, 100% of insulin was completely released within 10 hours. Thus, it could be seen that its bioavailability is significantly lower than that of the chitosan-phytic acid capsule prepared according to the present invention.

Experimental Example 8

Figure 17:
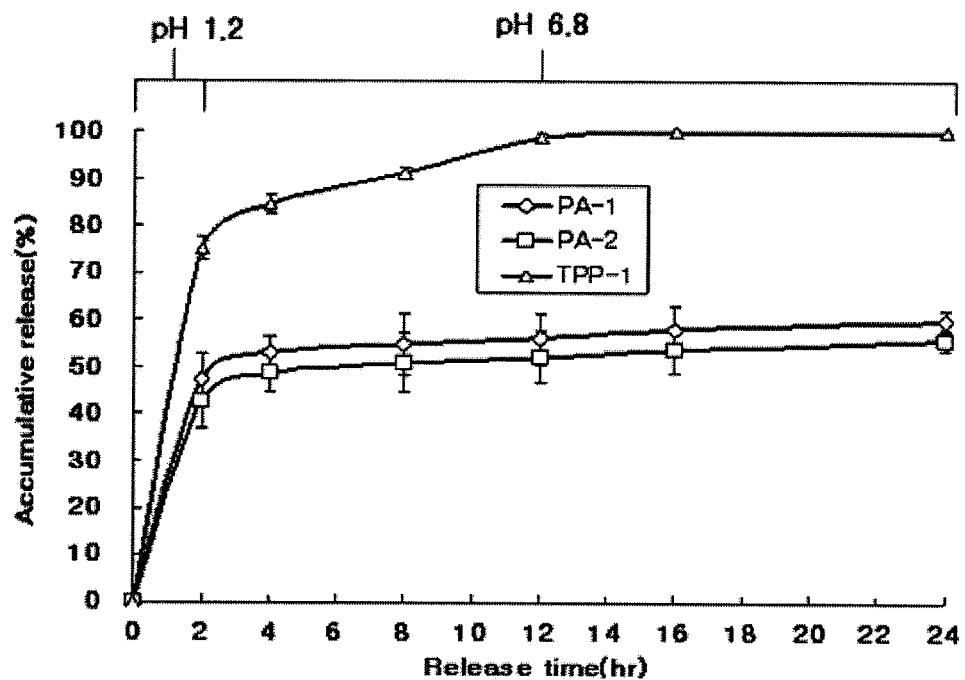
FIG. 17 a graph showing the release amount of insulin depending on time when two kinds of chitosan-phytic acid capsules prepared by using a 6% phytic acid solution with pH 1 and pH 6, respectively, according to the present invention and a chitosan-tripolyphosphate capsule prepared by using a 6% tripolyphosphate solution with pH 7 are treated with artificial gastric and intestinal juices.

Comparison of Bioavailability Between Chitosan-Phytic Acid Capsule and Chitosan-Tripolyphosphate Capsule The capsules showing the most preferable result were selected from Experimental Example 7 and Comparative Experimental Example 5, respectively, and compared. The results are shown in FIG. 17. The chitosan-phytic acid capsules prepared using a 6% phytic acid solution with pH 1 (PA-1) and pH 6 (PA-2), respectively, were selected in Experimental Example 7 and their results were shown in FIG. 17. The chitosan-tripolyphosphate capsule prepared using a 6% tripolyphosphate solution with pH 7 was selected in Comparative Experimental Example 5 and its result was shown in FIG. 17. It has been confirmed that the chitosan-phytic acid capsules release a smaller amount of insulin into the artificial gastric juice than the chitosan-tripolyphosphate capsule and gradually release the insulin into the artificial intestinal juice.

Preparative Example 4

Establishment of Diabetic Mouse

Six-week old Balb-c strain male mice were used. Streptozotocin was dissolved in a 0.1 mM sodium chloride buffer at a concentration of 30 mg/mL, followed by subcutaneously injecting into the male rats at a dosage of 65 mg/kg so as to induce diabetes. The male mice showing a blood glucose level of 470±40 mg/dL over two consecutive days were selected and the experiment was performed. The diabetic mice were starved for 12 hours before the experiment was started.

Experimental Example 9

Comparison of In Vivo Bioavailability of Chitosan Capsule Comprising Insulin

Figure 18:
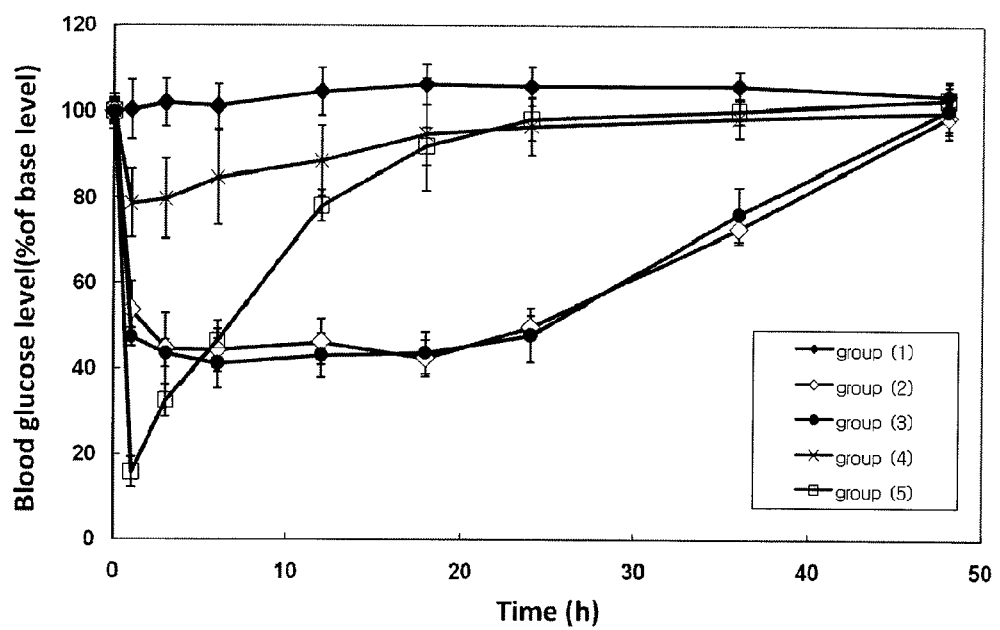
FIG. 18 is a graph showing a blood glucose level measured when two kinds of chitosan-phytic acid capsules prepared by using a 6% phytic acid solution with pH 1 and pH 6, respectively, according to the present invention and a chitosan-tripolyphosphate capsule prepared by using a 6% tripolyphosphate solution with pH 7 are orally administered to a diabetic mice, respectively.

After the capsules showing the most preferable result were selected from Experimental Example 7 and Comparative Experimental Example 5, respectively, each capsule was orally administered to the diabetic mouse established in Preparative Example 4 and a blood glucose level was measured. The results are shown in FIG. 18. Group (1) was a normal control to which saline was orally administered; Group (2) was the mouse to which the chitosan-phytic acid capsule comprising insulin (Experimental Example 7) prepared using a 6% phytic acid solution with pH 1 was orally administered (dosage: 40 IU/kg); Group (3) was the mouse to which the chitosan-phytic acid capsule comprising insulin (Experimental Example 7) prepared using a 6% phytic acid solution with pH 6 was orally administered (dosage: 40 IU/kg); Group (4) was the mouse to which the chitosan-tripolyphosphate capsule comprising insulin (Comparative Experimental Example 5) prepared using a 6% tripolyphosphate solution with pH 7 was orally administered (dosage: 40 IU/kg); and Group (5) was the mouse to which insulin was subcutaneously injected (dosage: 1 IU/kg) in order to compare the method of administering insulin according to the present invention with a conventional method thereof. As can be seen in FIG. 18, in case of administering insulin via a subcutaneous injection, the blood glucose level was rapidly decreased. Similarly, when the chitosan-phytic acid capsule was orally administered to the mouse, the blood glucose level was rapidly decreased. Further, in case of orally administering insulin using the chitosan-phytic acid capsule, the blood glucose level was maintained at a constant low level for 25 hours without being suddenly and excessively decreased. In case of orally administering insulin using the chitosan-tripolyphosphate capsule, the blood glucose level was also slightly decreased, but it was insignificant. Therefore, the usability and potentiality of the chitosan-phytic acid capsule as a delivery intermediator of an insulin agent for oral administration could be confirmed from the experimental results.

FIG. 19 numerically shows the results of the aforementioned experiment. AAC (area above the blood glucose level-time curve) is to be numerically expressed the area above the blood glucose level-time curve by using a linear trapezoidal rule. The larger an AAC value is, the more a drug is effective. Cmax designates a maximum value of decrease in blood glucose level in percentage, and the higher, the better within the range of a blood glucose level in which hypoglycemic shock is not induced. Tmax is a time required to reach Cmax, and the lower a Tmax value is, the more a drug is effective. F is relative bioavailability of a drug, which is calculated by multiplying the AAC value in case of the oral administration of insulin by the amount of insulin subcutaneously injected, dividing the resulting value by the AAC value in case of the subcutaneous injection of insulin, and dividing the resulting value by the amount of insulin orally administered. Therefore, as the F value is closer to 100%, the effect of a drug is stronger. As shown in FIG. 19, the AAC value measured in case of orally administering insulin using the chitosan-phytic acid capsule was about 2.6 times as high as that in case of subcutaneously injecting insulin, and its bioavailability was about 6 times as high as that in case of orally administering insulin using the chitosan-tripolyphosphate capsule. Thus, the possibility of the oral administration of insulin using the chitosan-phytic acid capsule could be confirmed once again.

Preparative Example 5

Preparation of Insulin-Chitosan Aqueous Solution

Insulin (Sigma-Aldrich) as a soluble active ingredient was dissolved in a 0.1 N HCl solution to have final concentrations of 4.4% (w/v) and 8.5% (w/v), respectively. Each insulin solution was added to the chitosan aqueous solution prepared in Preparative Example 1, stirred at 500 rpm for 10 minutes using a magnetic stirrer to disperse insulin, and then, left alone for a while to remove bubbles from the chitosan solution, to thereby obtain insulin-chitosan aqueous solutions.

Example 5

Preparation of Chitosan-Phytic Acid Capsule Comprising Insulin

The phytic acid aqueous solution at a concentration of 6% was prepared, and its pH was adjusted to 1, thereby preparing the capsule. Specifically, the phytic acid solution was added to distilled water and stirred to regulate the concentration of phytic acid to water, followed by regulating its pH using a 5.0 N sodium hydroxide solution. The insulin-chitosan aqueous solution prepared in Preparative Example 5 was added to the resulting solution drop by drop using a metering pump, and the resulting mixture was reacted to induce the binding between chitosan and phytic acid, thereby preparing the capsule. The prepared capsules were separated from the mixture, washed with distilled water two or three times, and then dried by a freeze-dry method. At this time, an initial freezing process was performed at −40° C. for 4 hours, followed by drying the capsules at −30° C. for 3 hours, −10° C. for 2 hours, 0° C. for 1 hour, 20° C. for 2 hours, and 30° C. for 5 hours.

Preparative Example 6

Establishment of Diabetic Rat

Male Sprague-Dawley (SD) rats of 250 to 280 g were used. Streptozotocin was dissolved in citric acid with pH 4.5 at a concentration of 50 mg/mL and administered to the rats for 2 days at a dosage of 50 mg/kg weight. Five days after, the rats showing a blood glucose level of 250 mg/dL or more were selected as diabetic rats.

Experimental Example 10

Comparison of In Vivo Effect of Lowering Blood Glucose Level According to Dosage of Chitosan-Insulin Capsule Since the preferable result was obtained in case of administering insulin at a dosage of 40 IU/kg in Experimental Example 9, the effect of the chitosan capsule on lowering a blood glucose level was examined according to a dosage of the chitosan-insulin capsule for 4 hours, wherein the chitosan-insulin capsule was prepared using the phytic acid solution with pH 1. The capsules prepared in Example 5 were orally administered to the diabetic rats established in Preparative Example 6 at a dosage of 10 IU/kg (L), 20 IU/kg (M) and 40 IU/kg (H), respectively. The capsules prepared using a 4.4% (w/w) insulin solution in Example 5 were administered to the rats at a dosage of 10 IU/kg (L) and 20 IU/kg (M), respectively, and the capsule prepared using a 8.5% (w/w) insulin solution was administered to the rat at a dosage of 40 IU/kg (H).

Figure 20:
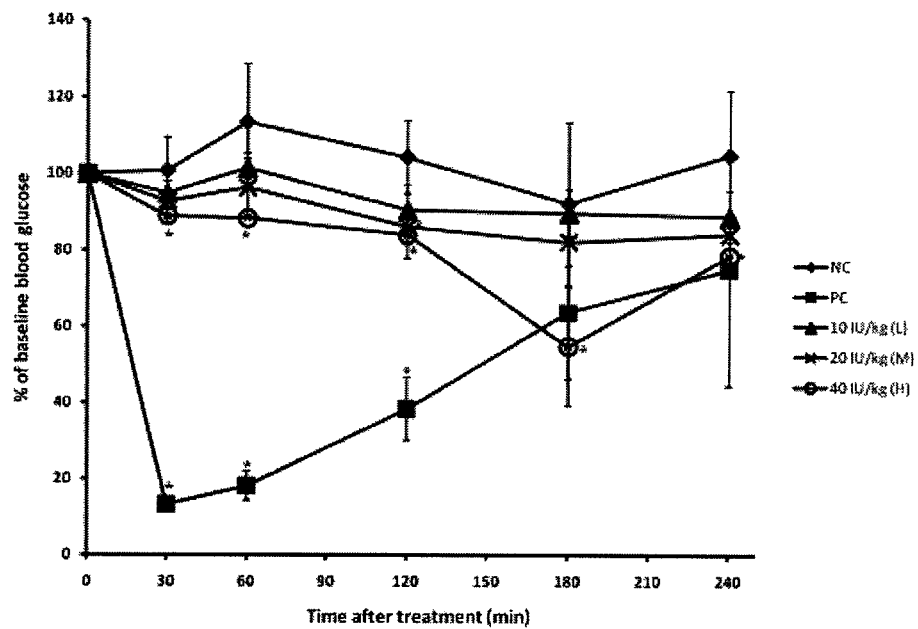
FIG. 20 is a graph showing a glucose lowering effect of a chitosan-insulin capsule depending on the dosage thereof for 4 hours after the chitosan-insulin capsule prepared by using a 6% phytic acid solution with pH 1 is orally administered to a diabetic rat.
Figure 21:
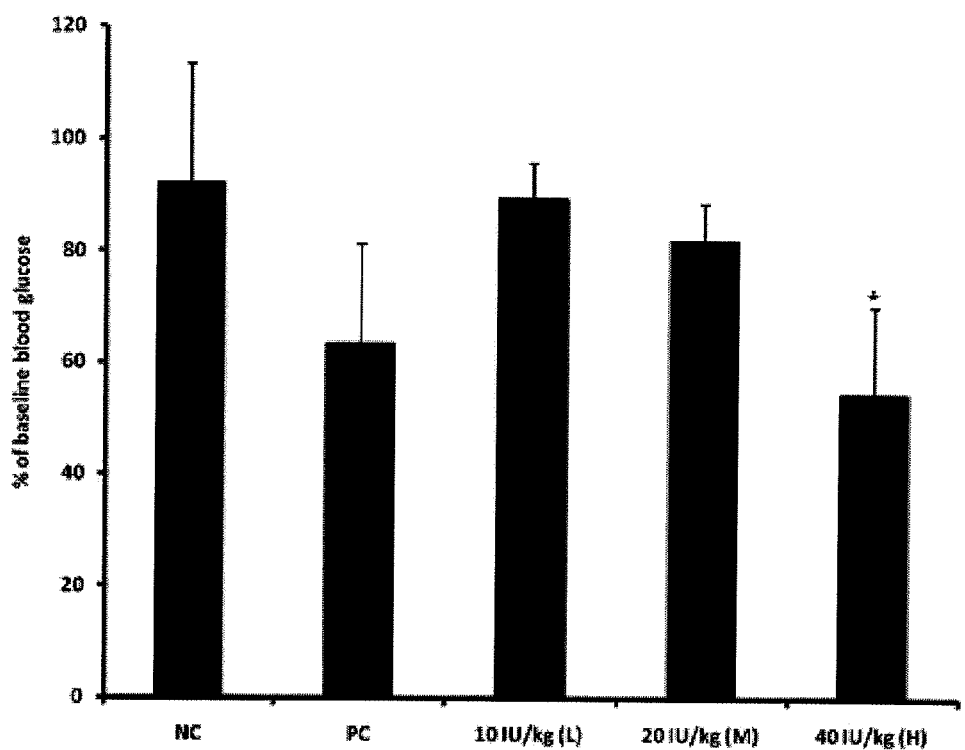
FIG. 21 is a graph showing a glucose lowering effect of a chitosan-insulin capsule depending on the dosage thereof 3 hours after the chitosan-insulin capsule prepared by using a 6% phytic acid solution with pH 1 is orally administered to a diabetic rat.

As shown in FIGS. 20 and 21, in case of subcutaneously injecting insulin (PC, positive control), the blood glucose level was most rapidly decreased. However, it could be confirmed that in case of orally administering 40 IU/kg of insulin using the chitosan-phytic acid capsule (H), 3 hours after the chitosan capsule was orally administered, the blood glucose level was lower than that of the subcutaneous injection of insulin. On the other hand, in case of orally administering the chitosan-phytic acid capsule comprising no insulin (NC, negative control), it has been confirmed that the blood glucose level did not decrease. Further, it has been confirmed that the oral administration of insulin using the chitosan-phytic acid capsule does not cause sudden and excessive decrease in the blood glucose level. Furthermore, such results were statistically meaningful, which demonstrates that the capsule in which phytic acid is used as a cross-linking agent can be effectively used.

Preparative Example 7

Preparation of Insulin-Chitosan Aqueous Solution

Insulin (Sigma-Aldrich) as a soluble active ingredient was dissolved in a 0.1 N HCl solution to have final concentrations of 3.7% (w/v) and 2.1% (w/v), respectively. Each insulin solution was added to the chitosan aqueous solution prepared in Preparative Example 1, stirred at 500 rpm for 10 minutes using a magnetic stirrer to disperse insulin, and then, left alone for a while to remove bubbles from the chitosan solution, to thereby obtain insulin-chitosan aqueous solutions.

Example 6

Preparation of Chitosan Capsule Comprising Insulin

The phytic acid aqueous solution at a concentration of 6% was prepared, and its pH was adjusted to 1, thereby preparing the capsule. Specifically, the phytic acid solution was added to distilled water and stirred to regulate the concentration of phytic acid to water, followed by regulating its pH using a 5.0 N sodium hydroxide solution. The insulin-chitosan aqueous solution prepared in Preparative Example 7 was added to the resulting solution drop by drop using a metering pump, and the resulting mixture was reacted to induce the binding between chitosan and phytic acid, thereby preparing the capsule. The prepared capsules were separated from the mixture, washed with distilled water two or three times, and then dried by a freeze-dry method. At this time, an initial freezing process was performed at −40° C. for 4 hours, followed by drying the capsules at −30° C. for 3 hours, −10° C. for 2 hours, 0° C. for 1 hour, 20° C. for 2 hours, and 30° C. for 5 hours.

Preparative Example 8

Establishment of Diabetic Rat

Male Wistar rats of 200 to 250 g were used. Streptozotocin was dissolved in citric acid with pH 4.5 at a concentration of 50 mg/mL and administered to the rats for 2 days at a dosage of 50 mg/kg weight. A week after, the rats showing a blood glucose level of 250 mg/dL or more were selected as diabetic rats.

Experimental Example 11

Figure 22:
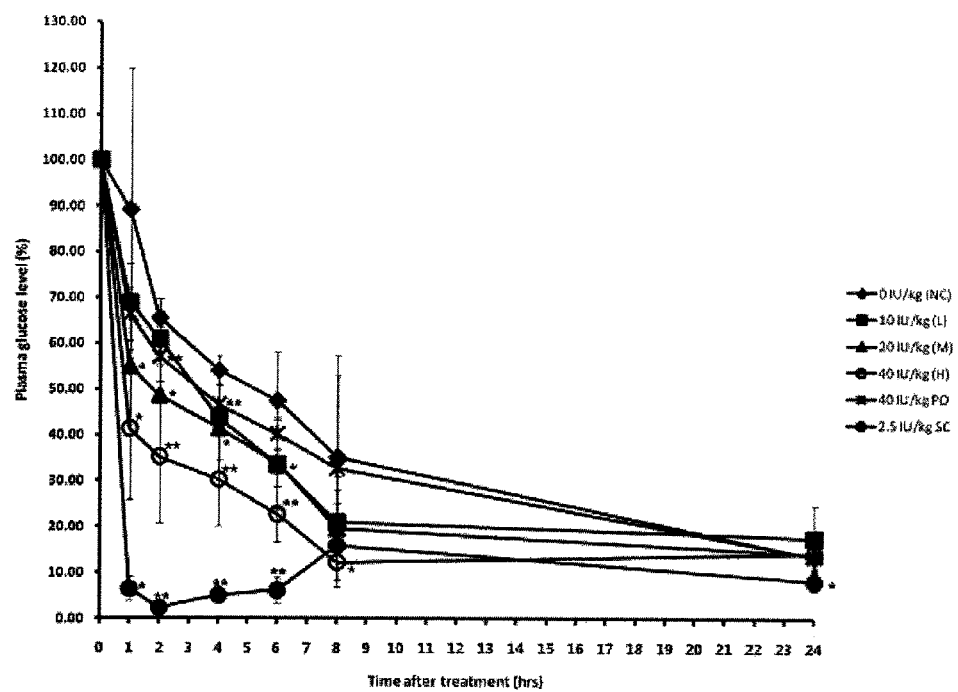
FIG. 22 is a graph showing a glucose lowering effect of a chitosan-insulin capsule depending on the dosage thereof for 24 hours after the chitosan-insulin capsule prepared by using a 6% phytic acid solution with pH 1 is orally administered to a diabetic rat.

Comparison of In Vivo Effect of Lowering Blood Glucose Level Depending on Dosage of Chitosan-Insulin Capsule Since the preferable result was obtained in case of administering insulin at a dosage of 40 IU/kg in Experimental Example 10, the effect of the chitosan capsule on lowering a blood glucose level was examined according to a dosage of the chitosan-insulin capsule for 24 hours, wherein the chitosan-insulin capsule was prepared using the phytic acid solution with pH 1. The capsules prepared in Example 6 were orally administered to the diabetic rats established in Preparative Example 8 at a dosage of 10 IU/kg, 20 IU/kg and 40 IU/kg, respectively, and the results are shown in FIG. 22. The capsules prepared using a 2.1% (w/w) insulin solution in Example 6 were orally administered to the rats at a dosage of 10 IU/kg (L) and 20 IU/kg (M), respectively, and the capsule prepared by using a 3.7% (w/w) insulin solution was orally administered to the rat at a dosage of 40 IU/kg (H).

As shown in FIG. 22, it could be confirmed that in case of administering the chitosan-insulin capsules at a dosage of 10 IU/kg, 20 IU/kg and 40 IU/kg, respectively, a decrease in blood glucose level is rapid and effective depending on the concentration. It has been also confirmed that such a lowering effect of a blood glucose level is maintained at least for 8 hours and statistically meaningful.

Preparative Example 9

Preparation of Growth Hormone-Chitosan Aqueous Solution

Human growth hormone (Vexxon) as a soluble active ingredient was dissolved in the deionized water to have a concentration of 2% (w/v). The solution was added to the chitosan aqueous solution prepared in Preparative Example 1, stirred at 500 rpm for 10 minutes using a magnetic stirrer to disperse growth hormone, and then, left alone for a while to remove bubbles from the chitosan solution, to thereby obtain a growth hormone-chitosan aqueous solution.

Example 7

Preparation of Chitosan-Phytic Acid Capsule Comprising Growth Hormone

The phytic acid aqueous solution at a concentration of 6% was prepared, and its pH was adjusted to 1, 2, 3, 4, 5, 6 and 7, respectively, to thereby prepare seven kinds of the capsules. Specifically, the phytic acid solution was added to distilled water and stirred to regulate the concentration of phytic acid to water, followed by regulating its pH using a 5.0 N sodium hydroxide solution. The growth hormone-chitosan aqueous solution prepared in Preparative Example 9 was added to the resulting solution drop by drop using a metering pump, and the resulting mixture was reacted to induce the binding between chitosan and phytic acid, thereby preparing the capsules. The prepared capsules were separated from the mixture, washed with distilled water two or three times, and then dried by a freeze-dry method. At this time, an initial freezing process was performed at −40° C. for 4 hours, followed by drying the capsules at −30° C. for 3 hours, −10° C. for 2 hours, 0° C. for 1 hour, 20° C. for 2 hours, and 30° C. for 5 hours.

Experimental Example 12

Growth Hormone Encapsulation Efficiency of Chitosan-Phytic Acid Capsule

Figure 23:
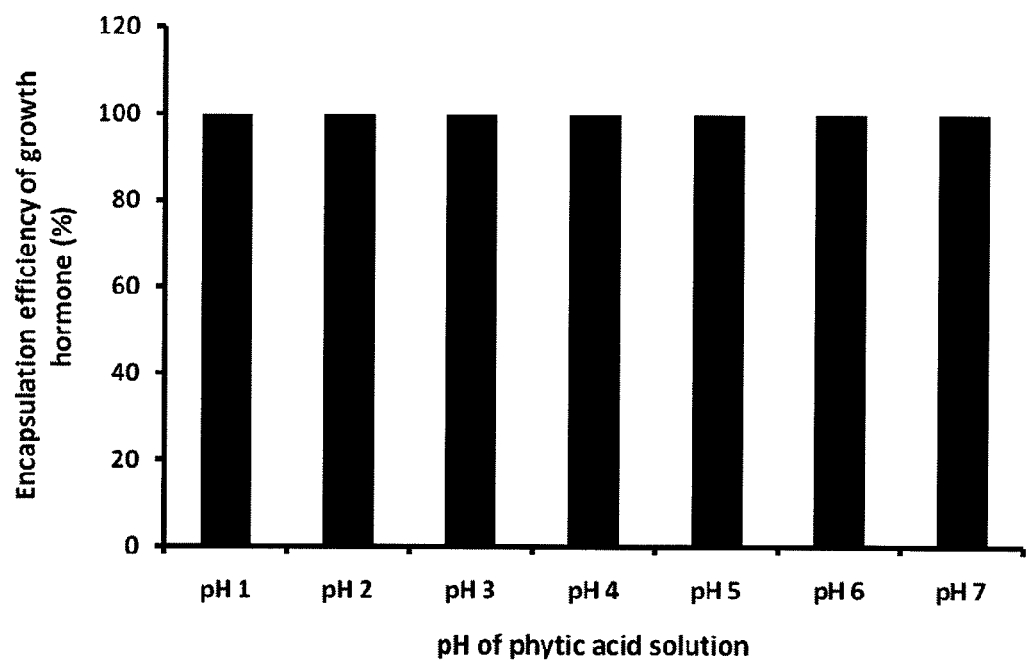
FIG. 23 is a graph showing a growth hormone encapsulation efficiency of a chitosan-phytic acid capsule depending on the acidity of a phytic acid solution when its concentration is 6%.

In order to measure the influence of a pH of a phytic acid aqueous solution on the degree of encapsulation, a growth hormone encapsulation efficiency of each capsule prepared in Example 7 was calculated. The amount of unencapsulated growth hormone remaining in the phytic acid solution after capsule formation was measured by HPLC, and a growth hormone encapsulation efficiency of the capsule was calculated by using the data. The results are shown in FIG. 23. As shown in FIG. 23, it could be confirmed that the growth hormone is completely encapsulated inside the capsule regardless of a pH of the phytic acid aqueous solution.

Experimental Example 13

Figure 24:
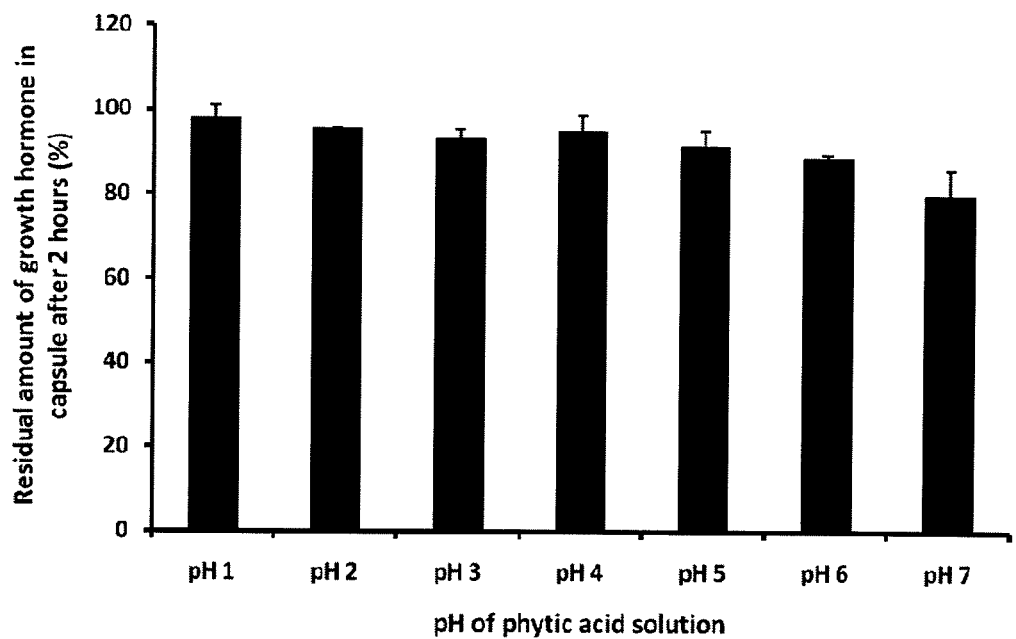
FIG. 24 is a graph showing the residual amount of growth hormone in a chitosan-phytic acid capsule depending on the acidity of a phytic acid solution 2 hours after the chitosan-phytic acid capsule is treated with an artificial gastric juice in case of a concentration of phytic acid of 6%.

Stability of Chitosan-Phytic Acid Capsule Comprising Growth Hormone in Artificial Gastric Juice Each capsule prepared in Example 7 was put into an artificial gastric juice (HCl 0.7% (v/v), NaCl 0.2% (w/v) in water) with pH 1.2 and shaken at 100 rpm for 2 hours in a 37° C. shaking incubator. Thereafter, the amount of growth hormone released into the artificial gastric juice was measured by HPLC. Using the data, after the treatment with the artificial gastric juice for 2 hours, the release amount of growth hormone thereinto was calculated, and the results are shown in FIG. 24. As shown in FIG. 24, it was observed that when the phytic acid solution has pH 1, growth hormone was almost never released into the artificial gastric juice, and the higher the acidity was, the more the growth hormone was released. However, it was confirmed that even in the capsule prepared using the phytic acid aqueous solution with pH 7, growth hormone was released below 30% into the artificial gastric juice. It has been confirmed from the results that the chitosan-phytic acid capsule prepared under lower pH conditions is more stable in the gastric juice under acidic conditions.

Experimental Example 14

Figure 25:
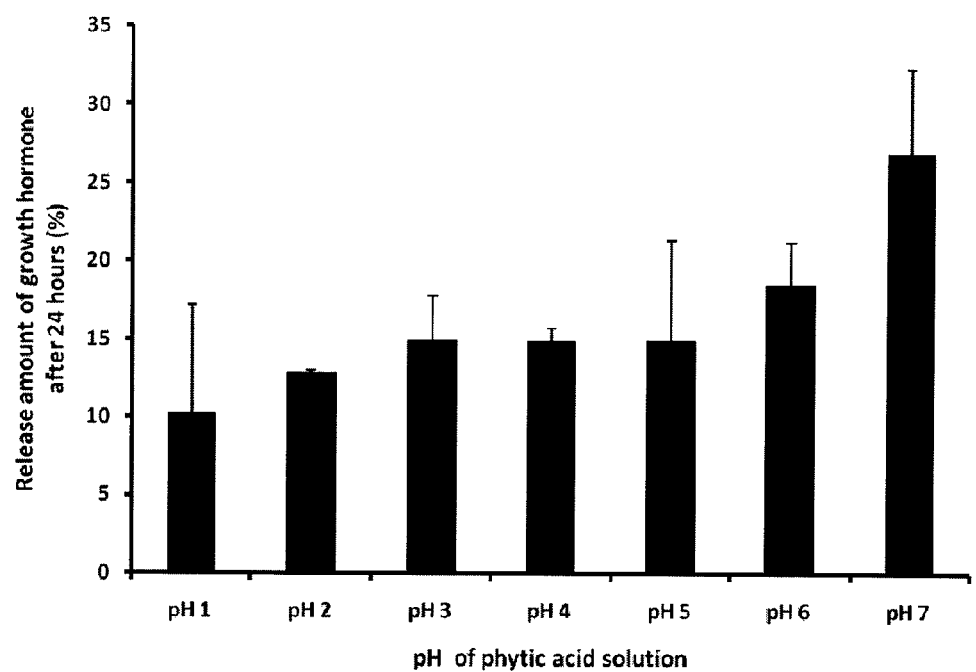
FIG. 25 is a graph showing the release amount of growth hormone depending on the acidity of a phytic acid solution 24 hours after a chitosan-phytic acid capsule prepared by using a 6% phytic acid solution under variable pH conditions of phytic acid solution is treated with artificial gastric and intestinal juices.

Measurement of Sustained-Release of Growth Hormone from Chitosan-Phytic Acid Capsule into Intestine In case of the encapsulated soluble active ingredient being absorbed through the intestinal wall, if the external wall of the capsule does not break down in the intestine, bioavailability of the soluble active ingredient encapsulated inside the capsule is deteriorated. Thus, in order to examine the bioavailability of the prepared capsule, an artificial gastric juice (pH 1.2) and an artificial intestinal juice (0.2 M $KH_2PO_4$ 25% (v/v), 0.2 N NaOH 11.8% (v/v) in water, pH 6.8) were prepared. Then, the release amount of growth hormone from the chitosan-phytic acid capsule prepared in Example 7 according to the present invention was measured. When the capsule was put in the artificial gastric juice identical to that of Experimental Example 2 and shaken at 100 rpm for 2 hours in a 37° C. shaking incubator, 30% or below of the encapsulated soluble active ingredient was released. The capsule put in the artificial gastric juice and shaken was put in the artificial intestinal juice and shaken at 37° C., 100 rpm. As shown in FIG. 25, in case of the chitosan-phytic capsule, the accumulated release amount of a soluble active ingredient was measured to be 5 to 35% after 24 hours. It could be confirmed that growth hormone is more released from the capsule prepared using the phytic acid having higher pH.

Figure 26:
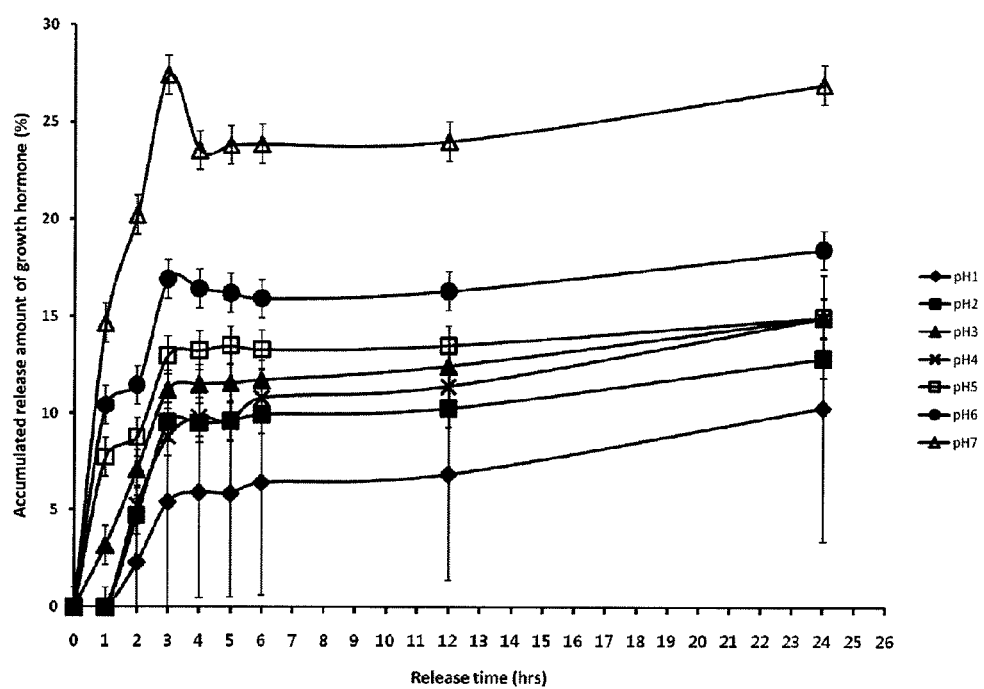
FIG. 26 is a graph showing the release amount of growth hormone depending on the acidity of a phytic acid solution in terms of time when a chitosan-phytic acid capsule prepared by using a 6% phytic acid solution under variable pH conditions of phytic acid solution is treated with artificial gastric and intestinal juices.

In order to measure the release amount of growth hormone depending on time, after the capsule was subjected to shaking incubation in the artificial gastric juice for 2 hours, the release amount of growth hormone was measured for total 24 hours in the artificial intestinal juice. As shown in FIG. 26, in the chitosan-phytic acid capsule prepared using the phytic acid having pH 1 to pH 4, growth hormone below 10% was released into the artificial gastric juice. Further, when the capsule was transferred to the artificial intestinal juice and further incubated, at most 20% of growth hormone was released thereinto.

The invention claimed is:

1. A method of preparing a chitosan capsule comprising:
reacting an aqueous chitosan solution containing a soluble active ingredient and a weak acid with an aqueous phytic acid solution to perform ionic gelation,
wherein the soluble active ingredient is insulin, albumin or growth hormone,
wherein the reaction is carried out by adding the aqueous chitosan solution containing the soluble active ingredient to the aqueous phytic acid solution in a dropping manner,
wherein the aqueous chitosan solution comprises the weak acid in a concentration ranging from 0.01 to 20%(w/v), and wherein the weak acid is one or more acids selected from the group consisting of acetic acid, lactic acid, citric acid, formic acid, ascorbic acid, oxalic acid, dilute hydrochloric acid and dilute sulfuric acid.

2. The method as claimed in claim 1, which further comprises a step of preparing an aqueous chitosan solution and a soluble active ingredient.

3. The method as claimed in claim 2, wherein the step comprises:
   (a) preparing a chitosan aqueous solution by adding chitosan to an aqueous solution;
   (b) preparing a soluble active ingredient aqueous solution; and
   (c) mixing the chitosan aqueous solution with the soluble active ingredient aqueous solution.

4. The method as claimed in claim 3, wherein the chitosan aqueous solution of step (a) comprises chitosan at a concentration ranging from 0.01 to 50%(w/v).

5. The method as claimed in claim 3, wherein the soluble active ingredient aqueous solution of step (b) comprises a soluble active ingredient at a concentration of 0.01%(w/v) or more.

6. The method as claimed in claim 1, wherein the phytic acid aqueous solution has a pH ranging from 0.5 to 7.

7. The method as claimed in claim 6, wherein the phytic acid aqueous solution has a pH ranging from 1 to 6.

8. The method as claimed in claim 1, wherein the phytic acid aqueous solution comprises phytic acid at a concentration of 0.1% (w/v) or more.

9. The method as claimed in claim 8, wherein the phytic acid aqueous solution comprises phytic acid at a concentration of 2% (w/v) or more.

10. The method as claimed in claim 1, which further comprises at least one step selected from the group consisting of separating the chitosan capsule, and washing and drying the same.

11. The method as claimed in claim 10, wherein the drying step is performed by freeze-drying.

* * * * *